United States Patent
Foshee, Jr. et al.

(10) Patent No.: US 11,278,731 B2
(45) Date of Patent: Mar. 22, 2022

(54) WEARABLE CARDIOVERTER DEFIBRILLATOR (WCD) SYSTEM INFORMING PATIENT THAT IT WILL NOT SHOCK RESPONSIVE TO JUST-SELF-TERMINATED CARDIAC ARRHYTHMIA

(71) Applicant: West Affum Holidings Corp., Grand Cayman (KY)

(72) Inventors: Phillip D. Foshee, Jr., Woodinville, WA (US); David P. Finch, Bothell, WA (US); Laura M. Gustavson, Redmond, WA (US); Nikolai Korsun, Lynnwood, WA (US); Joseph L. Sullivan, Kirkland, WA (US); Gregory T. Kavounas, Bellevue, WA (US)

(73) Assignee: West Affum Holdings Corp., Grand Cayman (KY)

( * ) Notice: Subject to any disclaimer, the term of this patent is extended or adjusted under 35 U.S.C. 154(b) by 154 days.

(21) Appl. No.: 16/568,954

(22) Filed: Sep. 12, 2019

(65) Prior Publication Data
US 2020/0001098 A1    Jan. 2, 2020

Related U.S. Application Data

(60) Continuation of application No. 15/673,184, filed on Aug. 9, 2017, now Pat. No. 10,426,966, which is a
(Continued)

(51) Int. Cl.
*A61N 1/39*    (2006.01)
*A61B 5/00*    (2006.01)
(Continued)

(52) U.S. Cl.
CPC .......... *A61N 1/3987* (2013.01); *A61B 5/318* (2021.01); *A61B 5/363* (2021.01); *A61B 5/6805* (2013.01);
(Continued)

(58) Field of Classification Search
CPC .. A61N 1/3987; A61N 1/3904; A61N 1/0484; A61N 1/3918; A61N 1/3968;
(Continued)

(56) References Cited

U.S. PATENT DOCUMENTS 3,724,355 A    4/1973    Unger
3,724,455 A    4/1973    Unger
(Continued)

FOREIGN PATENT DOCUMENTS

WO        9839061 A2     9/1998
WO    199803906 A2     9/1998

OTHER PUBLICATIONS

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, : loi:10.1093/eurheartj/ehl167, European Society of Cardiology.
(Continued)

*Primary Examiner* — Erin M Piateski
(74) *Attorney, Agent, or Firm* — Spectrum IP Law Group LLC

(57) ABSTRACT

In some embodiments, a wearable cardioverter defibrillator ("WCD") system comprises a support structure configured to be worn by a patient, a power source, an energy storage module configured to be coupled to the support structure, to be charged from the power source and to store an electrical charge, a discharge circuit coupled to the energy storage module, the discharge circuit controllable to discharge the
(Continued)

electrical charge so as to cause a shock to be delivered to the patient, a measurement circuit configured to render a physiological input from a patient physiological signal, a user interface configured to output one or more human-perceptible indications, and a processor. The processor can be configured to detect a cardiac arrhythmia of the patient from the physiological input, determine whether a type of the cardiac arrhythmia is at least one of a first type ("CA1") and a second type ("CA2"), if the type is CA1, cause a first human-perceptible indication to be output, else if the type is CA2, cause a second human-perceptible indication to be output, the second human-perceptible indication being different from the first human-perceptible indication, and then control the discharge circuit to deliver a shock responsive to the cardiac arrhythmia.

26 Claims, 16 Drawing Sheets

Related U.S. Application Data division of application No. 14/941,592, filed on Nov. 14, 2015, now Pat. No. 9,757,579, which is a continuation-in-part of application No. 14/461,670, filed on Aug. 18, 2014, now abandoned, and a continuation-in-part of application No. 14/743,882, filed on Jun. 18, 2015, now abandoned, which is a continuation of application No. 14/189,789, filed on Feb. 25, 2014, now Pat. No. 9,089,685.

(60) Provisional application No. 61/769,098, filed on Feb. 25, 2013.

(51) Int. Cl.
*A61N 1/04* (2006.01)
*A61B 5/0402* (2006.01)
*A61B 5/0464* (2006.01)
*A61B 5/318* (2021.01)
*A61B 5/363* (2021.01)

(52) U.S. Cl.
CPC .......... *A61B 5/7221* (2013.01); *A61N 1/0484* (2013.01); *A61N 1/3904* (2017.08); *A61N 1/3918* (2013.01); *A61N 1/3968* (2013.01); *A61N 1/39044* (2017.08)

(58) Field of Classification Search
CPC .... A61N 1/39044; A61B 5/318; A61B 5/363; A61B 5/6805; A61B 5/7221
USPC .......................................................... 607/5
See application file for complete search history.

(56) References Cited

U.S. PATENT DOCUMENTS

| | | | |
|---|---|---|---|
| 4,291,699 A | 9/1981 | Geddes et al. | |
| 4,583,524 A | 4/1986 | Hutchins | |
| 4,619,265 A | 10/1986 | Morgan et al. | |
| 4,895,151 A | 1/1990 | Grevis et al. | |
| 4,928,690 A | 5/1990 | Heilman et al. | |
| 4,955,381 A | 9/1990 | Way et al. | |
| 5,078,134 A | 1/1992 | Heilman et al. | |
| 5,201,992 A | 4/1993 | Andreadakis et al. | |
| 5,228,449 A | 7/1993 | Christ et al. | |
| 5,348,008 A | 9/1994 | Bornn et al. | |
| 5,353,793 A | 10/1994 | Bornn | |
| RE34,800 E | 11/1994 | Hutchins | |
| 5,394,892 A | 3/1995 | Kenny | |
| 5,405,362 A | 4/1995 | Kramer et al. | |
| 5,425,749 A | 6/1995 | Adams | |
| 5,474,574 A * | 12/1995 | Payne | A61N 1/3931 607/7 |
| 5,528,449 A | 6/1996 | Koch | |
| 5,601,612 A | 2/1997 | Gliner et al. | |
| 5,630,834 A | 5/1997 | Bardy | |
| 5,662,690 A | 9/1997 | Cole et al. | |
| 5,769,872 A | 6/1998 | Lopin et al. | |
| 5,782,878 A | 7/1998 | Morgan et al. | |
| 5,792,204 A | 8/1998 | Snell | |
| 5,803,927 A | 9/1998 | Cameron et al. | |
| 5,902,249 A | 5/1999 | Lyster | |
| 5,913,685 A | 6/1999 | Hutchins | |
| 5,944,669 A | 8/1999 | Kaib | |
| 6,047,203 A | 4/2000 | Sackner et al. | |
| 6,065,154 A | 5/2000 | Hulings et al. | |
| 6,068,651 A | 5/2000 | Brandell | |
| 6,108,197 A | 8/2000 | Janik | |
| 6,148,233 A | 11/2000 | Owen et al. | |
| 6,201,992 B1 | 3/2001 | Freeman | |
| 6,263,238 B1 | 7/2001 | Brewer et al. | |
| 6,287,328 B1 | 9/2001 | Snyder et al. | |
| 6,304,780 B1 | 10/2001 | Owen et al. | |
| 6,319,011 B1 | 11/2001 | Motli et al. | |
| 6,334,070 B1 | 12/2001 | Nova et al. | |
| 6,351,671 B1 | 2/2002 | Myklebust et al. | |
| 6,356,785 B1 | 3/2002 | Snyder et al. | |
| 6,427,083 B1 | 7/2002 | Owen et al. | |
| 6,437,083 B1 | 7/2002 | Owen et al. | |
| 6,529,875 B1 | 3/2003 | Nkajima | |
| 6,546,285 B1 | 4/2003 | Owen et al. | |
| 6,671,545 B2 | 12/2003 | Fincke | |
| 6,681,003 B2 | 1/2004 | Linder et al. | |
| 6,694,187 B1 | 2/2004 | Freeman | |
| 6,762,917 B1 | 7/2004 | Verbiest et al. | |
| 6,941,168 B2 | 9/2005 | Girouard | |
| 7,065,401 B2 | 6/2006 | Worden | |
| 7,149,576 B1 | 12/2006 | Baura et al. | |
| 7,336,994 B2 | 2/2008 | Hettrick et al. | |
| 7,559,902 B2 | 7/2009 | Ting et al. | |
| 7,865,238 B2 | 1/2011 | Brink | |
| 7,870,761 B2 | 1/2011 | Valemtine | |
| 7,894,894 B2 | 2/2011 | Stadler et al. | |
| 7,974,689 B2 | 7/2011 | Volpe et al. | |
| 8,036,746 B2 | 10/2011 | Sanders | |
| 8,135,462 B2 | 3/2012 | Owen et al. | |
| 8,140,154 B2 | 3/2012 | Donnelly et al. | |
| 8,369,944 B2 | 2/2013 | Macho et al. | |
| 8,548,557 B2 | 10/2013 | Garstka et al. | |
| 8,615,295 B2 | 12/2013 | Savage et al. | |
| 8,644,925 B2 | 2/2014 | Volpe et al. | |
| 8,825,154 B2 | 9/2014 | Jorgenson et al. | |
| 8,897,860 B2 | 11/2014 | Volpe et al. | |
| 8,904,214 B2 | 12/2014 | Volpe et al. | |
| 8,965,500 B2 | 2/2015 | Macho et al. | |
| 8,996,101 B2 | 3/2015 | Zhang et al. | |
| 9,008,801 B2 | 4/2015 | Kaib et al. | |
| 9,089,685 B2 | 7/2015 | Sullivan | |
| 9,131,901 B2 | 9/2015 | Volpe et al. | |
| 9,132,267 B2 | 9/2015 | Kaib | |
| 9,408,548 B2 | 8/2016 | Volpe et al. | |
| 9,454,219 B2 | 9/2016 | Volpe et al. | |
| 9,592,403 B2 | 3/2017 | Sullivan et al. | |
| 9,757,579 B2 | 9/2017 | Foshee et al. | |
| 10,016,614 B2 | 7/2018 | Sullivan et al. | |
| 10,426,966 B2 | 10/2019 | Foshee et al. | |
| 2003/0158593 A1 | 8/2003 | Heilman et al. | |
| 2004/0220623 A1 | 11/2004 | Hess | |
| 2005/0107833 A1 | 5/2005 | Freeman et al. | |
| 2005/0107834 A1 | 5/2005 | Freeman et al. | |
| 2006/0017575 A1 | 1/2006 | McAdams | |
| 2007/0179539 A1 | 8/2007 | Degroot et al. | |
| 2008/0208070 A1 | 8/2008 | Snyder et al. | |
| 2008/0215103 A1 | 9/2008 | Powers et al. | |
| 2008/0275519 A1 * | 11/2008 | Ghanem | A61N 1/3704 607/17 |
| 2008/0306560 A1 | 12/2008 | Macho et al. | |
| 2008/0312708 A1 | 12/2008 | Volpe et al. | |
| 2008/0312709 A1 | 12/2008 | Volpe et al. | |

(56) References Cited

U.S. PATENT DOCUMENTS

| | | |
|---|---|---|
| 2009/0005827 A1 | 1/2009 | Weintraub et al. |
| 2009/0018595 A1 | 1/2009 | Bharmi et al. |
| 2010/0007413 A1 | 1/2010 | Herleikson |
| 2010/0298899 A1 | 11/2010 | Donnelly et al. |
| 2010/0331904 A1 | 12/2010 | Warren et al. |
| 2011/0022105 A9 | 1/2011 | Owen et al. |
| 2011/0288604 A1 | 11/2011 | Kaib et al. |
| 2011/0288605 A1 | 11/2011 | Kalib et al. |
| 2012/0112903 A1 | 5/2012 | Kaib et al. |
| 2012/0144551 A1 | 6/2012 | Guldalian |
| 2012/0150008 A1 | 6/2012 | Kaib et al. |
| 2012/0158075 A1 | 6/2012 | Kaib et al. |
| 2012/0265265 A1 | 10/2012 | Razavi et al. |
| 2012/0283794 A1 | 11/2012 | Kaib et al. |
| 2012/0293323 A1 | 11/2012 | Kaib et al. |
| 2012/0302860 A1 | 11/2012 | Volpe et al. |
| 2012/0310315 A1 | 12/2012 | Savage et al. |
| 2013/0085538 A1 | 9/2013 | Volpe et al. |
| 2013/0231711 A1* | 9/2013 | Kaib ............ G16H 40/40 607/5 |
| 2013/0245388 A1 | 9/2013 | Rafferty et al. |
| 2013/0274565 A1 | 10/2013 | Langer et al. |
| 2013/0317852 A1 | 11/2013 | Worrell et al. |
| 2013/0325078 A1 | 12/2013 | Whiting et al. |
| 2014/0025131 A1 | 1/2014 | Sullivan et al. |
| 2014/0025132 A1 | 1/2014 | Libbus et al. |
| 2014/0070957 A1 | 3/2014 | Longinolli-Buitoni et al. |
| 2014/0091937 A1 | 4/2014 | Pratt et al. |
| 2014/0150781 A1 | 6/2014 | DiCapura et al. |
| 2014/0163663 A1 | 6/2014 | Poddar et al. |
| 2014/0276160 A1* | 9/2014 | Zhang ............ A61B 5/361 600/518 |
| 2014/0324112 A1 | 10/2014 | Macho et al. |
| 2014/0378812 A1 | 12/2014 | Saroka et al. |
| 2015/0039053 A1 | 2/2015 | Kaib et al. |
| 2015/0297107 A1 | 10/2015 | Sullivan et al. |
| 2015/0328472 A1 | 11/2015 | Sullivan et al. |
| 2016/0000349 A1 | 1/2016 | Sullivan et al. |
| 2016/0004831 A1 | 1/2016 | Carlson et al. |
| 2016/0015329 A1 | 1/2016 | Kohlrausch et al. |
| 2016/0082277 A1 | 3/2016 | Foshee et al. |
| 2016/0278698 A1 | 9/2016 | Freeman et al. |
| 2017/0056682 A1 | 3/2017 | Kumar et al. |

OTHER PUBLICATIONS

Lifecor LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Heartstart MRx and XL AED Algorithm—Application Nole, Jul. 2001, Edition 2 Philips Healthcare, USA.

The LifeVest Network/Patient Data Management System, Zoll, 2015, 20C0503 Rev A.

Pagan-Carlo, et al., "Encircling Overlapping Multipulse Shock Waveforms for Transthoracic Defibrillation," JACC Journals, Dec. 1998, vol. 32 Issue 7, pp. 2065-2071.

* cited by examiner

*SAMPLE COMPONENTS OF WEARABLE CARDIOVERTER DEFIBRILLATOR (WCD) SYSTEM*

SAMPLE COMPONENTS OF EXTERNAL DEFIBRILLATOR

WEARABLE CARDIOVERTER DEFIBRILLATOR (WCD) SYSTEM INFORMING PATIENT THAT IT WILL NOT SHOCK RESPONSIVE TO JUST-SELF-TERMINATED CARDIAC ARRHYTHMIA

CROSS REFERENCE TO RELATED PATENT APPLICATIONS

This patent application is a Continuation of U.S. patent application Ser. No. 15/673,184 filed Aug. 9, 2017, pending, which is a Divisional of U.S. patent application Ser. No. 14/941,592 filed Nov. 14, 2015, now U.S. Pat. No. 9,757,579, which in turn is a Continuation-In-Part of U.S. patent application Ser. No. 14/461,670 filed on Aug. 18, 2014, abandoned. Said application Ser. No. 14/941,592 is a Continuation-In-Part of U.S. patent application Ser. No. 14/743,882 filed on Jun. 18, 2015, abandoned, which is a continuation of U.S. patent application Ser. No. 14/189,789 filed on Feb. 25, 2014 now U.S. Pat. No. 9,089,685, and which in turn claimed benefit of U.S. Provisional patent application No. 61/769,098 filed on Feb. 25, 2013.

BACKGROUND

When people suffer from some types of heart arrhythmias, the result may be that blood flow to various parts of the body is reduced. Some arrhythmias may even result in a sudden cardiac arrest (SCA). SCA can lead to death very quickly, e.g. within 10 minutes, unless treated in the interim.

Some people have an increased risk of SCA. People at a higher risk include patients who have had a heart attack, or a prior SCA episode. A frequent recommendation is for these people to receive an implantable cardioverter defibrillator ("ICD"). The ICD is surgically implanted in the chest, and continuously monitors the patient's electrocardiogram ("ECG"). If certain types of heart arrhythmias are detected, then the ICD delivers an electric shock through the heart.

After being identified as having an increased risk of an SCA, and before receiving an ICD, these people are sometimes given a wearable cardioverter defibrillator ("WCD") system. (Earlier versions of such systems were called wearable cardiac defibrillator ("WCD") systems) A WCD system typically includes a harness, vest, or other garment that the patient is to wear. The WCD system includes a defibrillator and electrodes, coupled to the harness, vest, or other garment. When the patient wears the WCD system, the external electrodes may then make good electrical contact with the patient's skin, and therefore can help determine the patient's ECG. If a shockable heart arrhythmia is detected, then the defibrillator delivers the appropriate electric shock through the patient's body, and thus through the heart.

A challenge with prior art wearable cardioverter defibrillator ("WCD") systems is that, to be on the safe side, they shock the patient more times than is necessary—even when the patient is conscious and does not need a shock. In some instances, a patient may use a cancel switch to avert an impending shock, but even having to do that is a disruption, and can result in unwanted attention by others, loss of privacy and dignity, and so on.

BRIEF SUMMARY

The present description gives instances of wearable cardioverter defibrillator ("WCD") systems, storage media that store programs, and methods, the use of which may help overcome problems and limitations of the prior art.

In some embodiments, a wearable cardioverter defibrillator ("WCD") system may output an opening human-perceptible indication, after detecting a shockable cardiac arrhythmia but before validating it. This may succeed in informing the patient that the WCD system is working, and in particular analyzing a just-detected cardiac arrhythmia. The information may give comfort and confidence to the patient who may be conscious, and be experiencing only ventricular tachycardia but not ventricular fibrillation.

In some embodiments, a wearable cardioverter defibrillator ("WCD") system may output a closing human-perceptible indication, after detecting a shockable cardiac arrhythmia, and after further determining that it will not shock. This may succeed in informing the patient that the WCD system will not deliver a shock responsive to the cardiac arrhythmia, which may have just self-terminated. The information may give comfort to the patient who may be conscious, and may recognize that his or her ventricular tachycardia has self-terminated. Moreover, the patient will know that he or she will not be unnecessarily shocked while conscious, and will not even need to press a cancel switch.

In some embodiments, a wearable cardioverter defibrillator ("WCD") system may first determine whether or not the cardiac arrhythmia is validated, for example according to a validation criterion. If so, the WCD system may further determine whether or not the cardiac arrhythmia is confirmed according to a confirmation criterion, and then shock or not shock accordingly. This may reduce the incidence of unnecessary shocks to the patient.

In some embodiments, a wearable cardioverter defibrillator ("WCD") system may detect whether a cardiac arrhythmia is of a first type, such as ventricular fibrillation or fast ventricular tachycardia, or of a second type, such as slower ventricular tachycardia. If the cardiac arrhythmia is of the first type, the WCD system may shock anyway. If the cardiac arrhythmia is of the second type, however, the WCD system may determine whether or not the cardiac arrhythmia is confirmed, for example according to a confirmation criterion, and then shock or not shock accordingly. Thus, a WCD system made according to embodiments may autonomously shock a patient who is fibrillating, but not always if tachycardic, thus giving a chance to the tachycardia to self-terminate, without the patient needing to press a cancel switch.

In some embodiments, a wearable cardioverter defibrillator ("WCD") system may detect whether a cardiac arrhythmia is of a first type, such as ventricular fibrillation or fast ventricular tachycardia, or of a second type, such as slower ventricular tachycardia. The WCD system may validate the detected cardiac arrhythmia, and output a human-perceptible indication with a different delay, depending on the type of the detected cardiac arrhythmia.

In some embodiments, a wearable cardioverter defibrillator ("WCD") system may detect whether a cardiac arrhythmia is of a first type, such as ventricular fibrillation or fast ventricular tachycardia, or of a second type, such as slower ventricular tachycardia. The WCD system may output different human-perceptible indications, depending on the type of the detected cardiac arrhythmia.

These and other features and advantages of this description will become more readily apparent from the Detailed Description, which proceeds with reference to the associated drawings in which:

DETAILED DESCRIPTION

As has been mentioned, the present description is about wearable cardioverter defibrillator ("WCD") systems, storage media that store programs, and methods. Embodiments are now described in more detail.

A wearable cardioverter defibrillator ("WCD") system made according to embodiments has a number of components. These components can be provided separately as modules that can be interconnected, or can be combined with other components, etc.

A component of a WCD system can be a support structure, which is configured to be worn by the patient. The support structure can be any structure suitable for wearing, such as a harness, a vest, a half-vest—for example over the left side of the torso that positions electrodes on opposite sides of the heart, one or more belts that are configured to be worn horizontally or possibly vertically over a shoulder, another garment, and so on. The support structure can be implemented in a single component or multiple components. For example, a support structure may have a top component resting on the shoulders, for ensuring that the defibrillation electrodes will be in the appropriate positions for defibrillating, and a bottom component resting on the hips, for carrying the bulk of the weight of the defibrillator. A single component embodiment could be with a belt around at least the torso. Other embodiments could use an adhesive structure or another way for attaching to the patient, without encircling any part of the body. There can be other examples.

Figure 1:
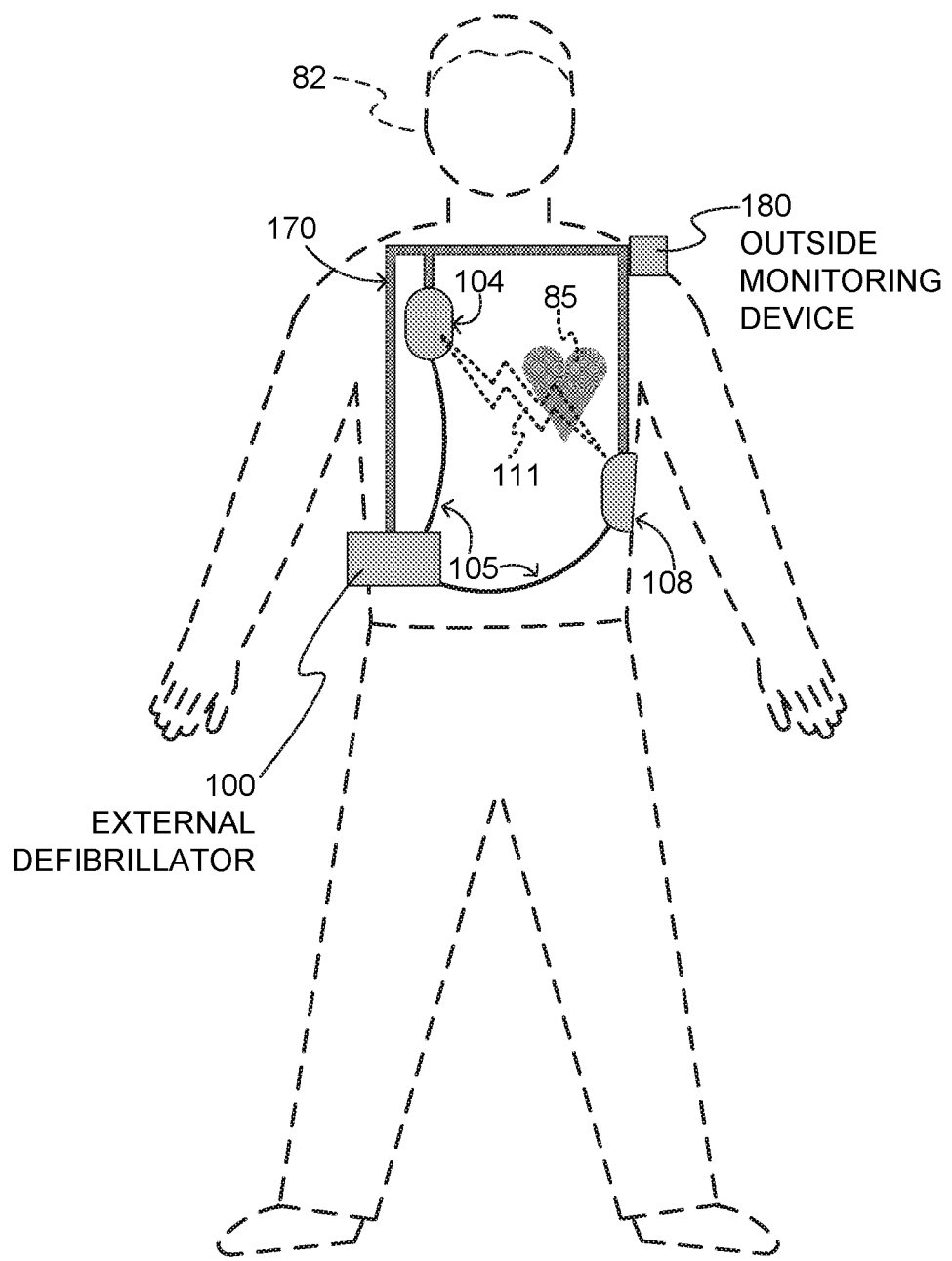
FIG. 1 is a diagram of components of a sample wearable cardioverter defibrillator ("WCD") system, made according to embodiments.

FIG. 1 depicts components of a WCD system made according to embodiments, as it might be worn by a patient 82. A patient such as patient 82 may also be referred to as a person and/or wearer, since that patient wears components of the WCD system.

In FIG. 1, a generic support structure 170 is shown relative to the body of patient 82, and thus also relative to his or her heart 85. Structure 170 could be a harness, a vest, a half-vest, one or more belts, or a garment, etc., as per the above. Structure 170 could be implemented in a single component, or multiple components, and so on. Structure 170 is wearable by patient 82, but the manner of wearing it is not depicted, as structure 170 is depicted only generically in FIG. 1.

A WCD system according to embodiments is configured to defibrillate a patient who is wearing it, by delivering an electrical charge to the patient's body in the form of an electric shock delivered in one or more pulses. FIG. 1 shows a sample external defibrillator 100, and sample defibrillation electrodes 104, 108, which are coupled to external defibrillator 100 via electrode leads 105. Defibrillator 100 and defibrillation electrodes 104, 108 are coupled to support structure 170. As such, many of the components of defibrillator 100 can be therefore coupled to support structure 170. When defibrillation electrodes 104, 108 make good electrical contact with the body of patient 82, defibrillator 100 can administer, via electrodes 104, 108, a brief, strong electric pulse 111 through the body. Pulse 111, also known as a defibrillation shock or therapy shock, is intended to go through and restart heart 85, in an effort to save the life of patient 82. Pulse 111 can further include one or more pacing pulses, and so on.

A prior art defibrillator typically decides whether to defibrillate or not based on an ECG signal of the patient. However, defibrillator 100 can defibrillate, or not defibrillate, also based on other inputs.

The WCD system may optionally include an outside monitoring device 180. Device 180 is called an "outside" device because it is provided as a standalone device, for example not within the housing of defibrillator 100. Device 180 can be configured to monitor at least one local parameter. A local parameter can be a parameter of patient 82, or a parameter of the WCD system, or a parameter of the environment, as will be described later in this document.

Optionally, device 180 is physically coupled to support structure 170. In addition, device 180 can be communicatively coupled with other components, which are coupled to support structure 170. Such communication can be implemented by a communication module, as will be deemed applicable by a person skilled in the art in view of this disclosure.

Figure 2:
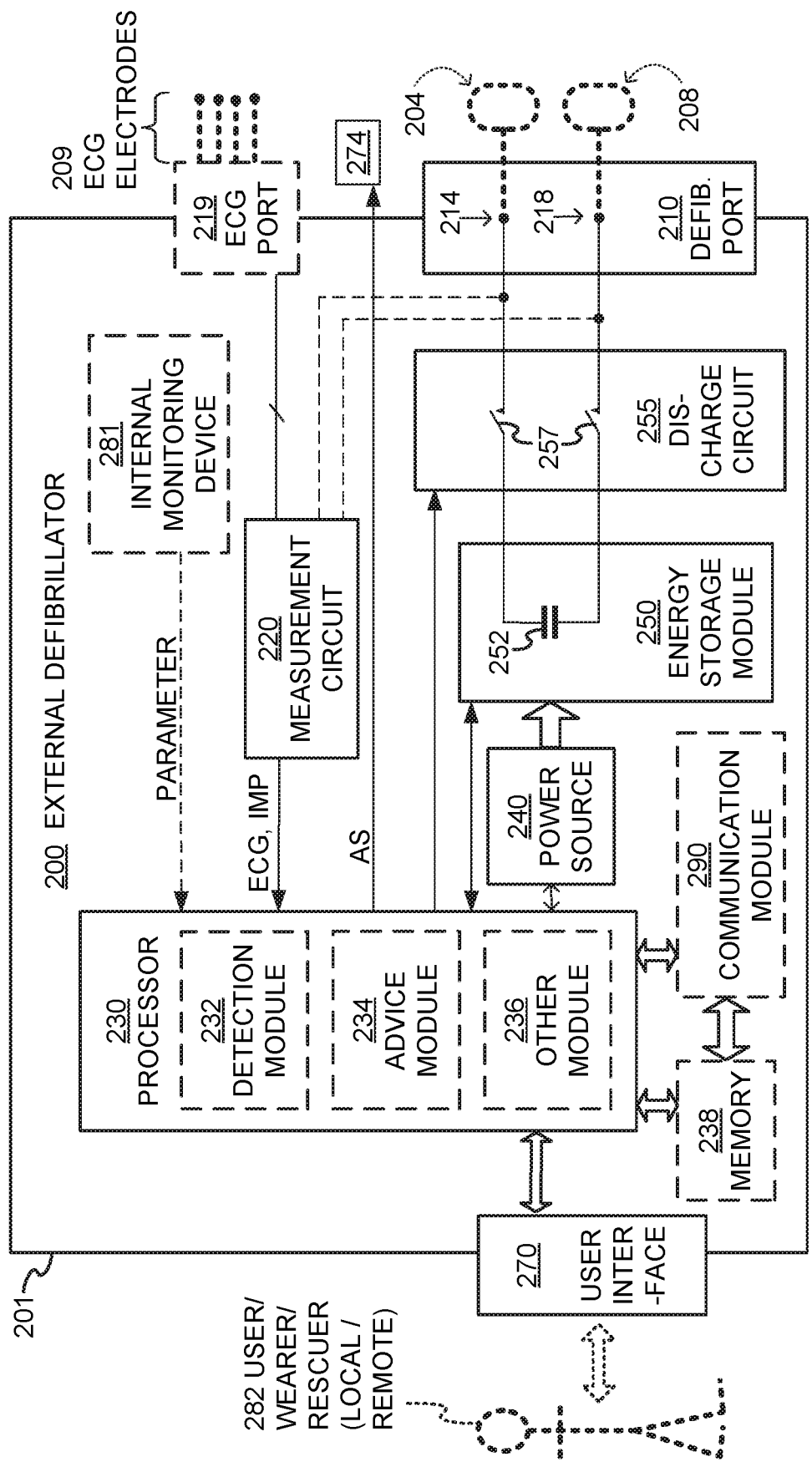
FIG. 2 is a diagram showing sample components of an external defibrillator, such as the one belonging in the system of FIG. 1, and which is made according to embodiments.

FIG. 2 is a diagram showing components of an external defibrillator 200, made according to embodiments. These components can be, for example, included in external defibrillator 100 of FIG. 1. The components shown in FIG. 2 can be provided in a housing 201, which is also known as casing 201.

External defibrillator 200 is intended for a patient who would be wearing it, such as patient 82 of FIG. 1. Defibrillator 200 may further include a user interface 270 for a user 282. User 282 can be patient 82, also known as wearer 82. Or user 282 can be a local rescuer at the scene, such as a bystander who might offer assistance, or a trained person. Or, user 282 might be a remotely located trained caregiver in communication with the WCD system.

User interface 270 can be made in any number of ways. User interface 270 may include output devices, which can be visual, audible or tactile, for communicating to a user. For example, an output device can be a light, or a screen to display what is detected and measured, and provide visual feedback to rescuer 282 for their resuscitation attempts, and so on. Another output device can be a speaker, which can be configured to issue voice prompts, etc. Sounds, lights, images, vibrations, and anything that can be perceived by user 282 can also be called human-perceptible indications. In diagrams that accompany the present description, a "human-perceptible indication" may be abbreviated as "HPI". User interface 270 may also include input devices for receiving inputs from users. Such input devices may additionally include various controls, such as pushbuttons, keyboards, touchscreens, a microphone, and so on. An input device can be a cancel switch, which is sometimes called a "live-man" switch and a divert button. In some embodiments, actuating the cancel switch can prevent the impending delivery of a shock.

Defibrillator 200 may include an internal monitoring device 281. Device 281 is called an "internal" device because it is incorporated within housing 201. Monitoring device 281 can monitor patient parameters, patient physiological parameters, system parameters and/or environmental parameters, all of which can be called patient data. In other words, internal monitoring device 281 can be complementary or an alternative to outside monitoring device 180 of FIG. 1. Allocating which of the system parameters are to be monitored by which monitoring device can be done according to design considerations.

Patient physiological parameters include, for example, those physiological parameters that can be of any help in detecting by the wearable defibrillation system whether the patient is in need of a shock, plus optionally their medical history and/or event history. Examples of such parameters include the patient's ECG, blood oxygen level, blood flow, blood pressure, blood perfusion, pulsatile change in light transmission or reflection properties of perfused tissue, heart sounds, heart wall motion, breathing sounds and pulse. Accordingly, the monitoring device could include a perfusion sensor, a pulse oximeter, a Doppler device for detecting blood flow, a cuff for detecting blood pressure, an optical sensor, illumination detectors and perhaps sources for detecting color change in tissue, a motion sensor, a device that can detect heart wall movement, a sound sensor, a device with a microphone, an SpO2 sensor, and so on. Pulse detection is taught at least in Physio-Control's U.S. Pat. No. 8,135,462, which is hereby incorporated by reference in its entirety. In addition, a person skilled in the art may implement other ways of performing pulse detection.

In some embodiments, the local parameter is a trend that can be detected in a monitored physiological parameter of patient 82. A trend can be detected by comparing values of parameters at different times. Parameters whose detected trends can particularly help a cardiac rehabilitation program include: a) cardiac function (e.g. ejection fraction, stroke volume, cardiac output, etc.); b) heart rate variability at rest or during exercise; c) heart rate profile during exercise and measurement of activity vigor, such as from the profile of an accelerometer signal and informed from adaptive rate pacemaker technology; d) heart rate trending; e) perfusion, such as from SpO2 or CO2; f) respiratory function, respiratory rate, etc.; g) motion, level of activity; and so on. Once a trend is detected, it can be stored and/or reported via a communication link, along perhaps with a warning. From the report, a physician monitoring the progress of patient 82 will know about a condition that is either not improving or deteriorating.

Patient state parameters include recorded aspects of patient 82, such as motion, posture, whether they have spoken recently plus maybe also what they said, and so on, plus optionally the history of these parameters. Or, one of these monitoring devices could include a location sensor such as a global positioning system ("GPS") location sensor. Such a sensor can detect the location, plus a speed can be detected as a rate of change of location over time. Many motion detectors output a motion signal that is indicative of the motion of the detector, and thus of the patient's body. Patient state parameters can be very helpful in narrowing down the determination of whether SCA is indeed taking place.

A WCD system made according to embodiments may include a motion detector. In embodiments, a motion detector can be implemented within monitoring device 180 or monitoring device 281. Such a motion detector can be configured to detect a motion event. In response, the motion detector may render or generate from the detected motion event a motion detection input that can be received by a subsequent device or functionality. A motion event can be defined as is convenient, for example a change in motion from a baseline motion or rest, etc. Such a motion detector can be made in many ways as is known in the art, for example by using an accelerometer.

System parameters of a WCD system can include system identification, battery status, system date and time, reports of self-testing, records of data entered, records of episodes and intervention, and so on.

Environmental parameters can include ambient temperature and pressure. A humidity sensor may provide information as to whether it is likely raining. Presumed patient location could also be considered an environmental parameter. The patient location could be presumed if monitoring device 180 or 281 includes a GPS location sensor as per the above.

Defibrillator 200 typically includes a defibrillation port 210, such as a socket in housing 201. Defibrillation port 210 includes electrical nodes 214, 218. Leads of defibrillation electrodes 204, 208, such as leads 105 of FIG. 1, can be plugged into defibrillation port 210, so as to make electrical contact with nodes 214, 218, respectively. It is also possible that defibrillation electrodes 204, 208 are connected continuously to defibrillation port 210, instead. Either way, defibrillation port 210 can be used for guiding, via electrodes, to the wearer the electrical charge that has been stored in energy storage module 250. The electric charge will be the shock for defibrillation, pacing, and so on.

Defibrillator 200 may optionally also have an ECG port 219 in housing 201, for plugging in sensing electrodes 209, which are also known as ECG electrodes and ECG leads. It is also possible that sensing electrodes 209 can be connected continuously to ECG port 219, instead. Sensing electrodes 209 can help sense an ECG signal, e.g. a 12-lead signal, or a signal from a different number of leads, especially if they make good electrical contact with the body of the patient. Sensing electrodes 209 can be attached to the inside of support structure 170 for making good electrical contact with the patient, similarly as defibrillation electrodes 204, 208.

Optionally a WCD system according to embodiments also includes a fluid that it can deploy automatically between the electrodes and the patient skin. The fluid can be conductive, such as by including an electrolyte, for making a better electrical contact between the electrode and the skin. Electrically speaking, when the fluid is deployed, the electrical impedance between the electrode and the skin is reduced. Mechanically speaking, the fluid may be in the form of a low-viscosity gel, so that it does not flow away, after it has been deployed. The fluid can be used for both defibrillation electrodes 204, 208, and sensing electrodes 209.

The fluid may be initially stored in a fluid reservoir, not shown in FIG. 2, which can be coupled to the support structure. In addition, a WCD system according to embodiments further includes a fluid deploying mechanism 274. Fluid deploying mechanism 274 can be configured to cause at least some of the fluid to be released from the reservoir, and be deployed near one or both of the patient locations, to which the electrodes are configured to be attached to the patient. In some embodiments, fluid deploying mechanism 274 is activated responsive to receiving activation signal AS from processor 230, prior to the electrical discharge.

Defibrillator 200 also includes a measurement circuit 220. Measurement circuit 220 receives physiological signals of the patient from ECG port 219, if provided. Even if defibrillator 200 lacks ECG port 219, measurement circuit 220 can obtain physiological signals through nodes 214, 218 instead, when defibrillation electrodes 204, 208 are attached to the patient. In these cases, the patient's ECG signal can be sensed as a voltage difference between electrodes 204, 208. Plus, impedance between electrodes 204, 208 and/or the connections of ECG port 219 can be sensed. Sensing the impedance can be useful for detecting, among other things, whether these electrodes 204, 208 and/or sensing electrodes 209 are not making good electrical contact with the patient's body. These patient physiological signals can be sensed, when available. Measurement circuit 220 can then render or generate information about them as physiological inputs, data, other signals, etc. More strictly speaking, the information rendered by measurement circuit 220 is output from it, but this information can be called an input because it is received by a subsequent device or functionality as an input.

Defibrillator 200 also includes a processor 230. Processor 230 may be implemented in any number of ways. Such ways include, by way of example and not of limitation, digital and/or analog processors such as microprocessors and digital signal processors ("DSP"s); controllers such as microcontrollers; software running in a machine; programmable circuits such as field programmable gate arrays ("FPGA"s), field-programmable analog arrays ("FPAA"s), programmable logic devices ("PLD"s), application specific integrated circuits ("ASIC"s), any combination of one or more of these, and so on.

Processor 230 can be considered to have a number of modules. One such module can be a detection module 232. Detection module 232 can include a ventricular fibrillation ("VF") detector. The patient's sensed ECG from measurement circuit 220, which can be available as physiological inputs, data, or other signals, may be used by the VF detector to determine whether the patient is experiencing VF. Detecting VF is useful, because VF results in SCA. Detection module 232 can also include a ventricular tachycardia ("VT") detector, and so on.

Another such module in processor 230 can be an advice module 234, which generates advice for what to do. The advice can be based on outputs of detection module 232. There can be many types of advice according to embodiments. In some embodiments, the advice is a shock/no shock determination that processor 230 can make, for example via advice module 234. The shock/no shock determination can be made by executing a stored Shock Advisory Algorithm. A Shock Advisory Algorithm can make a shock/no shock determination from one or more of ECG signals that are captured according to embodiments, and determining whether a shock criterion is met. The determination can be made from a rhythm analysis of the captured ECG signal or otherwise.

In some embodiments, when the decision is to shock, an electrical charge is delivered to the patient. Delivering the electrical charge is also known as discharging. Shocking can be for defibrillation, pacing, and so on.

Processor 230 can include additional modules, such as other module 236, for other functions. In addition, if internal monitoring device 281 is indeed provided, it may be operated in part by processor 230, etc.

Defibrillator 200 optionally further includes a memory 238, which can work together with processor 230. Memory 238 may be implemented in any number of ways. Such ways include, by way of example and not of limitation, volatile memories, nonvolatile memories ("NVM"), read-only memories ("ROM"), random access memories ("RAM"), magnetic disk storage media, optical storage media, smart cards, flash memory devices, any combination of these, and so on. Memory 238 is thus a non-transitory storage medium. Memory 238, if provided, can include programs for processor 230, which processor 230 may be able to read and execute. More particularly, the programs can include sets of instructions in the form of code, which processor 230 may be able to execute upon reading. Executing is performed by physical manipulations of physical quantities, and may result in functions, processes, actions and/or methods to be performed, and/or the processor to cause other devices or components or blocks to perform such functions, processes, actions and/or methods. The programs can be operational for the inherent needs of processor 230, and can also include protocols and ways that decisions can be made by advice module 234. In addition, memory 238 can store prompts for user 282, if this user is a local rescuer. Moreover, memory 238 can store data. The data can include patient data, system data and environmental data, for example as learned by internal monitoring device 281 and outside monitoring device 180. The data can be stored in memory 238 before it is transmitted out of defibrillator 200, or stored there after it is received by defibrillator 200.

Defibrillator 200 may also include a power source 240. To enable portability of defibrillator 200, power source 240 typically includes a battery. Such a battery is typically implemented as a battery pack, which can be rechargeable or not. Sometimes a combination is used of rechargeable and non-rechargeable battery packs. Other embodiments of power source 240 can include an AC power override, for where AC power will be available, an energy storage capacitor, and so on. In some embodiments, power source 240 is controlled by processor 230.

Defibrillator 200 additionally includes an energy storage module 250, which can thus be coupled to the support structure of the WCD system. Module 250 is where some electrical energy is stored in the form of an electrical charge, when preparing it for discharge to administer a shock. Module 250 can be charged from power source 240 to the right amount of energy, as controlled by processor 230. In typical implementations, module 250 includes a capacitor 252, which can be a single capacitor or a system of capacitors, and so on. As described above, capacitor 252 can store the energy in the form of an electrical charge, for delivering to the patient.

Defibrillator 200 moreover includes a discharge circuit 255. When the decision is to shock, processor 230 can be configured to control discharge circuit 255 to discharge through the patient the electrical charge stored in energy storage module 250. When so controlled, circuit 255 can permit the energy stored in module 250 to be discharged to nodes 214, 218, and from there also to defibrillation electrodes 204, 208, so as to cause a shock to be delivered to the patient. Circuit 255 can include one or more switches 257. Switches 257 can be made in a number of ways, such as by an H-bridge, and so on. Circuit 255 can also be controlled via user interface 270.

Defibrillator 200 can optionally include a communication module 290, for establishing one or more wired or wireless communication links with other devices of other entities, such as a remote assistance center, Emergency Medical Services ("EMS"), and so on. Module 290 may also include an antenna, portions of a processor, and other sub-components as may be deemed necessary by a person skilled in the art. This way, data and commands can be communicated, such as patient data, event information, therapy attempted, CPR performance, system data, environmental data, and so on.

Defibrillator 200 can optionally include other components.

Returning to FIG. 1, in embodiments, one or more of the components of the shown WCD system have been customized for patient 82. This customization may include a number of aspects. For instance, support structure 170 can be fitted to the body of patient 82. For another instance, baseline physiological parameters of patient 82 can be measured, such as the heart rate of patient 82 while resting, while walking, motion detector outputs while walking, etc. Such baseline physiological parameters can be used to customize the WCD system, in order to make its diagnoses more accurate, since bodies behave differently. For example, such parameters can be stored in a memory of the WCD system, and so on.

A programming interface can be made according to embodiments, which receives such measured baseline physiological parameters. Such a programming interface may input automatically in the WCD system the baseline physiological parameters, along with other data.

Figure 3A:
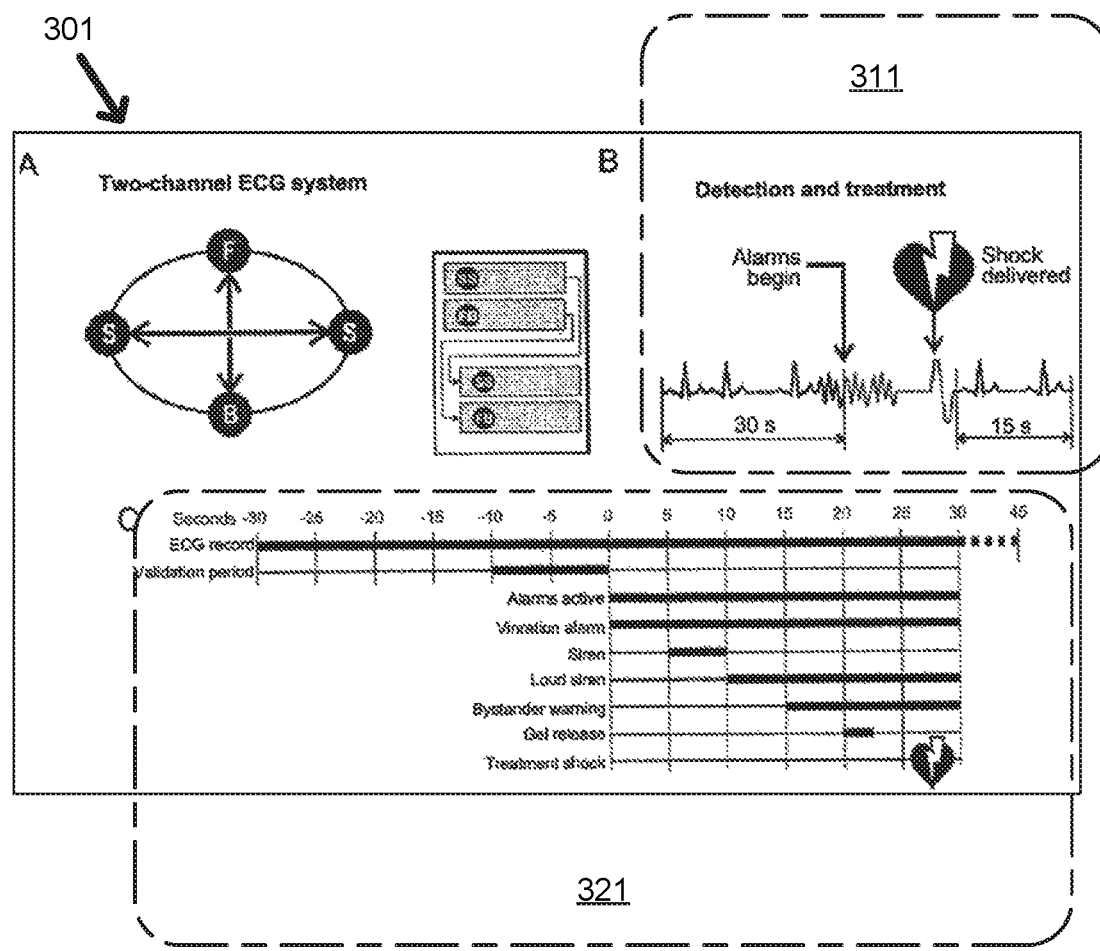
FIG. 3A is a rendering of diagram in a publication that describes characteristics of a WCD system in the prior art, with annotations.

FIG. 3A is a rendering of diagram in a publication that describes characteristics of a WCD system in the prior art, with annotations added in this document. In particular, FIG. 3A is labeled "FIG. 3" in that publication, which is: KLEIN Helmut U., GOLDENBERG Ilan & MOSS Arthur J., Risk stratification for implantable cardioverter defibrillator therapy: the role of the wearable cardioverter-defibrillator, European Heart Journal, 2013, pp. 1-14, doi:10.1093/eurheartj/eht167.

In FIG. 3A, the diagram of the prior art is designated in the rectangle 301. It purports to describe the detection, treatment and alarm system of a prior art WCD system. Attention is drawn to designated sections 311, 321 of this diagram.

Figure 3B:
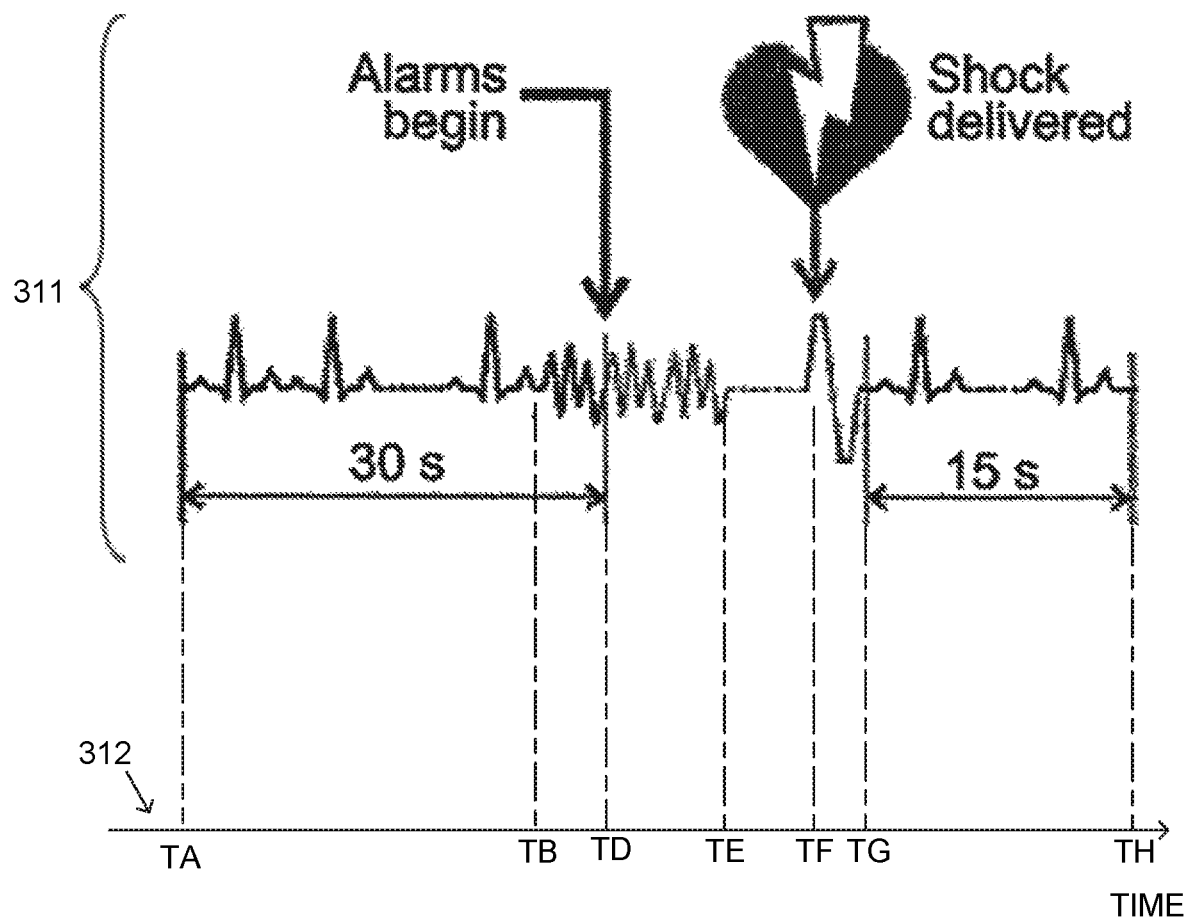
FIG. 3B shows a magnification of a section of the prior art diagram of FIG. 3A, with further annotations along an added time axis.

FIG. 3B shows a magnification of designated section 311 of the prior art diagram of FIG. 3A, with further annotations along an added time axis 312. Section 311 is characterized as detection time, shock delivery, and electrocardiogram recording after shock delivery. In the added time axis 312, certain events of section 311 have intercepts TA, TB, TD, TE, TF, TG, TH as shown, for easier reference.

Figure 3C:
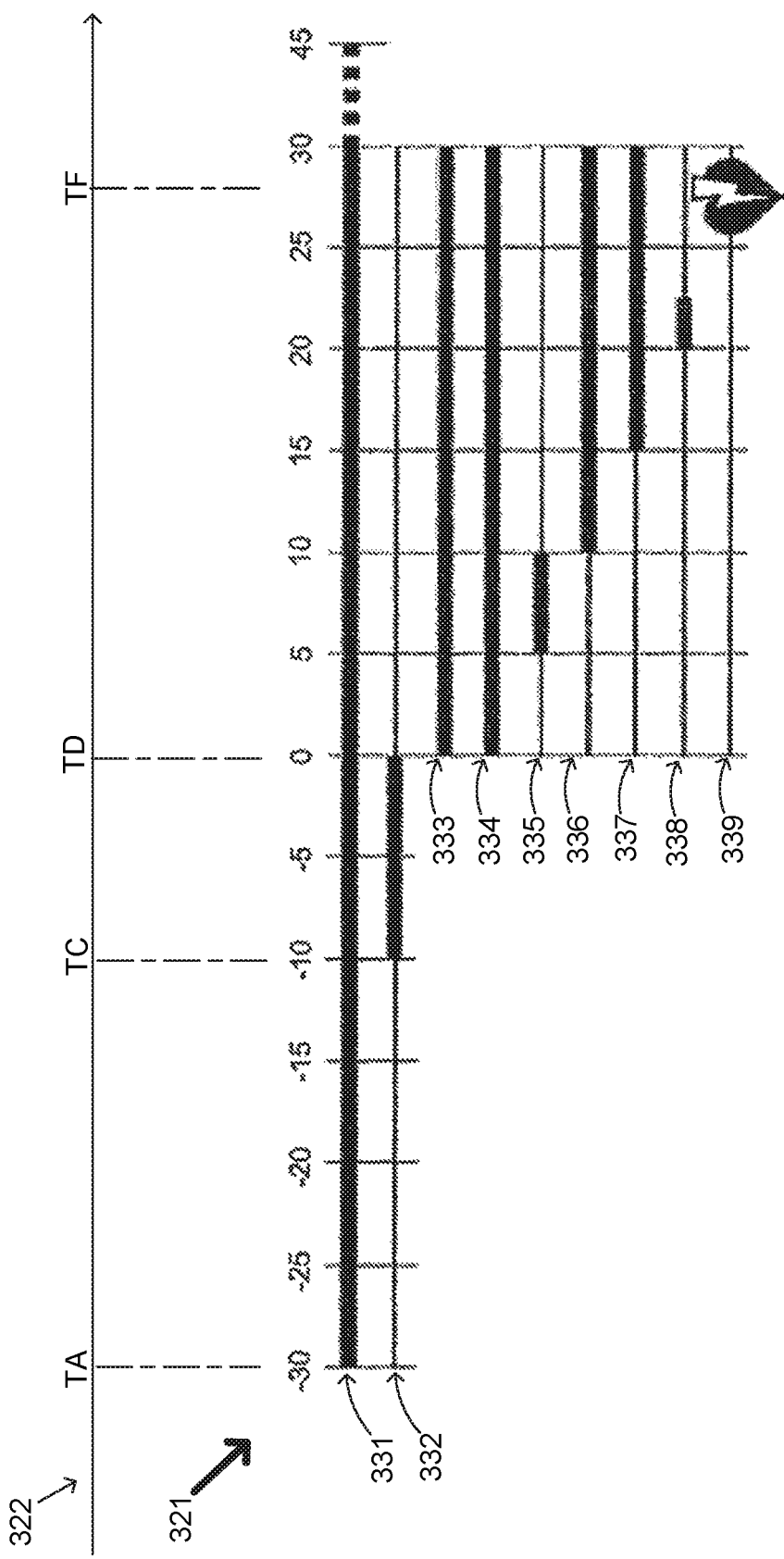
FIG. 3C shows a magnification of a section of the prior art diagram of FIG. 3A, with further annotations along an added time axis.

FIG. 3C shows a magnification of designated section 321 of the prior art diagram of FIG. 3A, with further annotations along an added time axis 322. Section 321 is characterized as the time sequence of alarms, etc. In particular, timeline 331 is characterized as ECG record, timeline 332 is characterized as Validation period, timeline 333 is characterized as Alarms active, timeline 334 is characterized as Vibration alarm, timeline 335 is characterized as Siren, timeline 336 is characterized as Loud siren, timeline 337 is characterized as Bystander warning, timeline 338 is characterized as Gel release, and timeline 339 is characterized as Treatment shock.

In FIG. 3C, in the added time axis 322, certain events of section 321 have intercepts TA, TC, TD, TF as shown, for easier reference. Some of these are the same time intercepts as those in time axis 312 of FIG. 3B. In addition, time intercept TB of FIG. 3B could be the same as time intercept TC of FIG. 3C.

As mentioned above, embodiments of the invention include systems, processors and methods. The devices and/or systems mentioned in this document perform functions, processes and/or methods. These functions, processes and/or methods may be implemented by one or more devices that include logic circuitry. Such a device can be alternately called a computer, and so on. It may be a standalone device or computer, such as a general purpose computer, or part of a device that has one or more additional functions. The logic circuitry may include a processor and non-transitory computer-readable storage media, such as memories, of the type described elsewhere in this document. Often, for the sake of convenience only, it is preferred to implement and describe a program as various interconnected distinct software modules or features. These, along with data are individually and also collectively known as software. In some instances, software is combined with hardware, in a mix called firmware.

Moreover, methods and algorithms are described below. These methods and algorithms are not necessarily inherently associated with any particular logic device or other apparatus. Rather, they are advantageously implemented by programs for use by a computing machine, such as a general-purpose computer, a special purpose computer, a microprocessor, a processor such as described elsewhere in this document, and so on.

This detailed description includes flowcharts, display images, algorithms, and symbolic representations of program operations within at least one computer readable medium. An economy is achieved in that a single set of flowcharts is used to describe both programs, such that can be executed by a processor, and also methods. So, while flowcharts described methods in terms of boxes, they also concurrently describe programs.

Methods are now described.

In some embodiments, a WCD system may output an opening human-perceptible indication, after detecting a shockable cardiac arrhythmia but before completing its analysis of the cardiac arrhythmia, for instance before validating the cardiac arrhythmia. Examples are now described.

Figure 4:
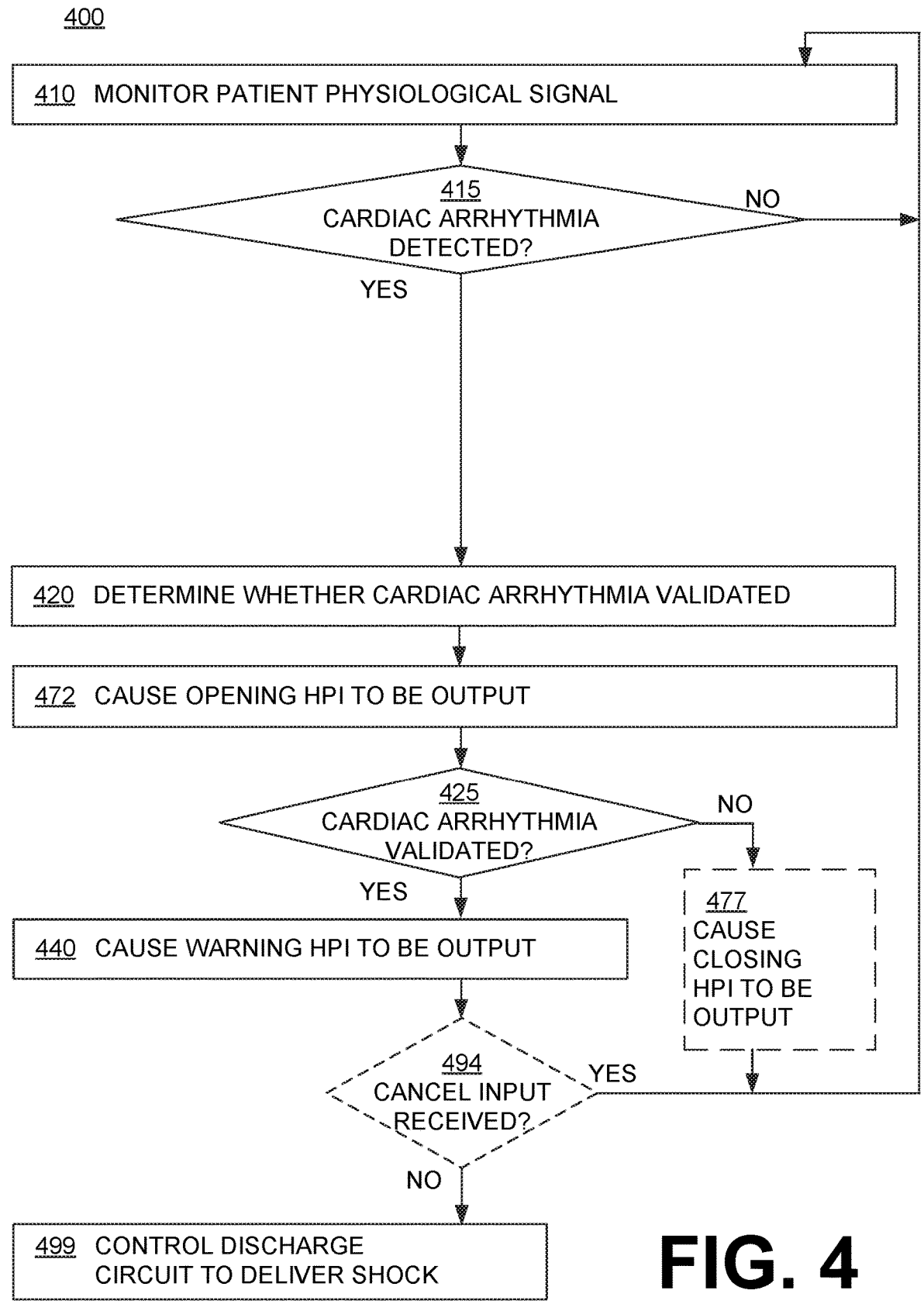
FIG. 4 is a flowchart for illustrating methods according to embodiments.
Figure 5:
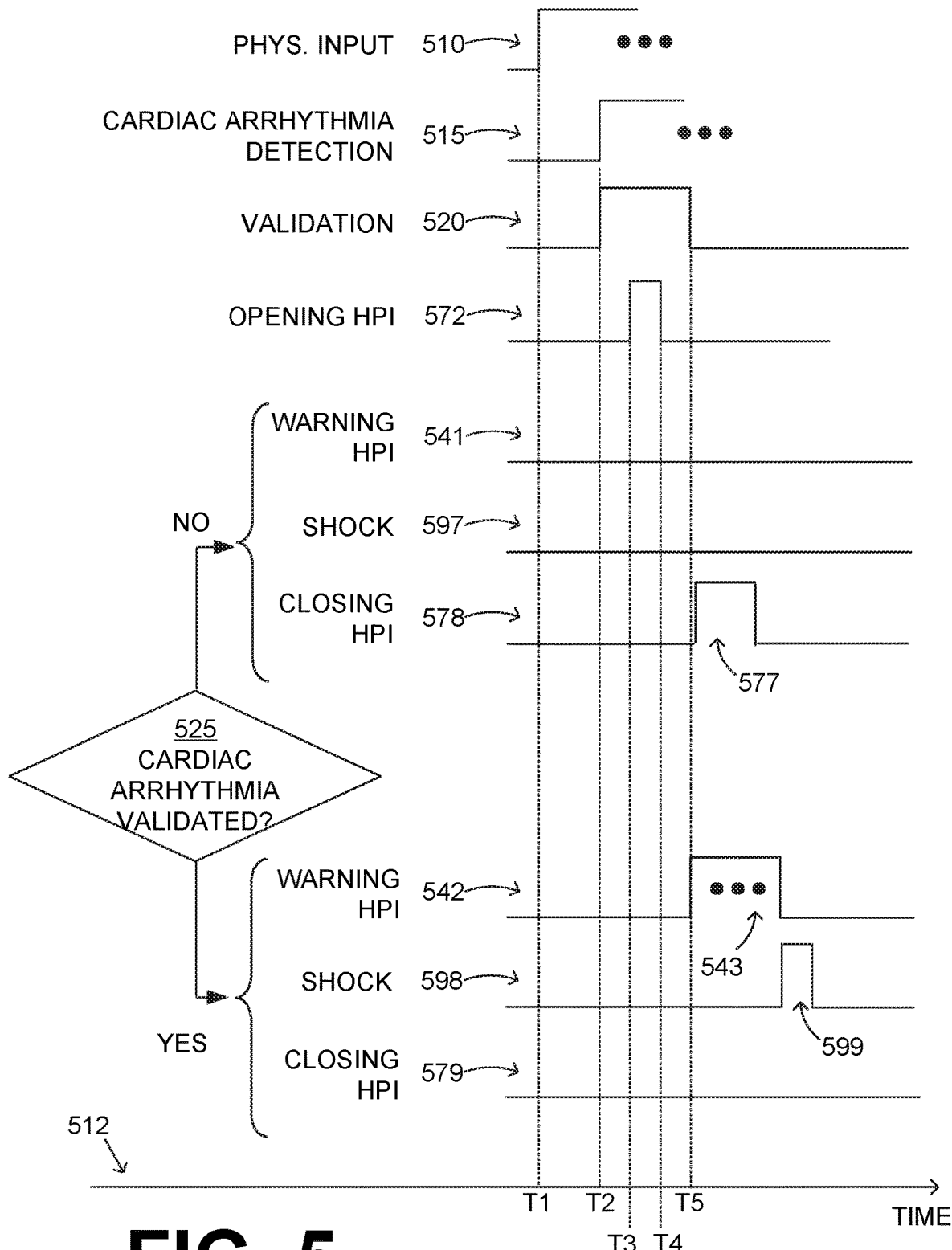
FIG. 5 is a time diagram of a sample series of events that may result from methods of the flowchart of FIG. 4.

FIG. 4 shows a flowchart 400 for describing methods according to embodiments. In addition, FIG. 5 is a time diagram of a sample series of events that may result from methods of the flowchart of FIG. 4. Of course, a different series of events may result from the methods of the flowchart of FIG. 4. The events of FIG. 5 are shown along a time axis 512, with intercepts that are not to scale. This portion of this description proceeds by referring to both diagrams.

According to an operation 410 of FIG. 4, a patient physiological signal may be monitored. The physiological signal can be the patient's electrocardiogram ("ECG"), impedance, blood pressure, blood oxygen saturation, and so on. As mentioned previously, measurement circuit 220, or equivalently another transducer, may render a physiological input from the monitored patient physiological signal. In FIG. 5, a timeline 510 indicates that the physiological input starts being received at a time T1, by switching from a low value to a high value.

According to another operation 415 of FIG. 4, it is inquired whether a cardiac arrhythmia is detected from the physiological input. It will be understood that this means a cardiac arrhythmia of interest, namely a shockable cardiac arrhythmia such as VF or VT. A difference between VF and VT is that the patient becomes unconscious very soon after VF starts, while the patient may remain conscious throughout a VT episode, whether prolonged or not. As will be seen, embodiments may provide a longer confirmation period for VT than VF, which works well with the fact that VT sometimes self-terminates, while VF almost never does.

While at operation 415 no cardiac arrhythmia is being detected, execution returns to operation 410. This cardiac arrhythmia detection is shown in FIG. 5 along a timeline 515. There is no detection while timeline 515 has a low value. Detection may happen at time T2, at which time timeline 515 changes to a high value.

Returning to FIG. 4, if detection happens at operation 415 then, according to another operation 420, it can be determined whether or not the cardiac arrhythmia is validated, for example according to a validation criterion, meaning depending on whether or not the validation criterion is met. For example, the validation criterion may include that the detected cardiac arrhythmia needs to be maintained for a threshold validation time. Operation 420 may need some time to be performed.

In addition, according to another operation 472, an opening human-perceptible indication ("HPI") may be caused to be output responsive to detecting the cardiac arrhythmia. This opening HPI may be caused to be output prior to completing the determination of operation 420. Accordingly, the execution of operations 420, 472 may overlap in time at least in part. In the example of FIG. 5, timeline 520 shows validation being performed between times T2 and T5. Moreover, timeline 572 shows an example of when the opening HPI is performed, and in particular lasting between times T3 and T4. This opening HPI may be caused to be output at a time T3, which is prior to completing the determination of operation 420 at time T5.

It will be appreciated that, if the patient is having a VF episode, he or she might be unconscious and never perceive this opening HPI. On the other hand, if the patient's arrhythmia is a VT episode, he or she may well be conscious and perceive their own arrhythmia.

In embodiments where this opening HPI is caused to be output prior to completing the determination of operation 420, the system might not know yet whether it will shock the patient or not. Indeed, if the cardiac arrhythmia turns out to be a mild VT, and the patient is still conscious, perhaps a shock will not be called for, eventually. A longer threshold validation time may be called for, during which the VT may self-terminate. As will be seen later in this document, in some embodiments where the VT is detected to self-terminate, no shock is administered to the conscious patient. Of course, if the VT becomes fast VT and degenerates into VF, a shock will be needed.

Since this opening HPI is caused to be output prior to completing the determination of operation 420, in some embodiments this opening HPI may fulfill the function of giving comfort and confidence to the patient that their WCD system is working, while they do not have to do anything, such as immediately stopping what they are doing to frantically search for the cancel switch so as to avoid a shock while conscious. Nor will they be embarrassed in front of others, if the opening HPI is discreet, and the cardiac arrhythmia eventually self-terminates. The opening HPI might give such comfort and confidence to a person who is having a sustained episode of low-rate VT that causes them to feel uncomfortable ("crummy"), even though they don't need to be shocked. Such an episode may self-terminate. In addition, the opening HPI might give such comfort and confidence to someone who learns news that excites them, such as by watching a sports event. Such a person may experience a high-rate supra-ventricular (SVT) rhythm that can make them feel crummy as well, even though they don't need to be shocked, either.

In order to give the patient this comfort and confidence, the opening HPI may communicate to the patient that at least some analysis will be performed on the cardiac arrhythmia, for example to determine whether or not it is validated. Such communicating may be explicit, for example by the opening HPI including a voice message to the effect of "HAVE DETECTED ARRHYTHMIA OF YOUR HEART, AND NOW VALIDATING IT". Alternately, an opening HPI can be more discreet, so that only the patient will perceive it. Such a more discreet opening HPI can be a tactile signal like a vibration, whose meaning the patient will have been trained to understand. For example, the opening HPI can be a group of three consecutive vibrations, perhaps each having the same duration. Of course, the vibrations will have to be designed to be intense enough and prolonged enough to be perceptible by a patient above and beyond their possible VT, given that a VT is itself a vibration within their body.

In some instances, the determination of operation 420 may take longer, for example longer than 30 sec. In such cases, the opening HPI may be extended, for the patient's confidence in the WCD to be sustained through the validation process. In some embodiments, the opening HPI may be caused to be output for as long as operation 420 is being performed, but that is not an example of FIG. 5, where the time T4 ends before time T5. To extend the example above, the group of three vibrations may be repeated every 7 to 10 sec.

Subsequent operations may depend on the determination of whether or not the cardiac arrhythmia is so validated. According to another operation 425 of FIG. 4, if it is determined that the cardiac arrhythmia is not so validated, execution may return to operation 410. Where it is written in this document that it is determined that the cardiac arrhythmia is or is not so validated, it means to be or not be validated according to the previously mentioned validation criterion, the determination of such validation, etc.

When according to operation 425 it is determined that the cardiac arrhythmia is not so validated, execution may return to operation 410 by further optionally executing another operation 477. According to operation 477, a closing HPI is caused to be output, in a manner and for an effect that are described later in this document for an operation 677 of FIG.

6. In such a case, the discharge circuit can be controlled to not deliver a shock for some time, e.g. at least 25 min from when the opening HPI was caused to be output at operation 472 of FIG. 4, because the patient may not need a shock for that time, or for that event.

In FIG. 5, box 525 can be another example of box 425. If it is determined that the cardiac arrhythmia is not so validated, timeline 541 indicates that no warning HPI is caused to be output and timeline 597 indicates that no shock is delivered. In addition, timeline 578 indicates that a closing HPI event 577 may be caused to be output, such as by operation 477.

Returning to FIG. 4, if at operation 425 it is determined that the cardiac arrhythmia is so validated then, according to another operation 440, a warning HPI can be caused to be output. The warning HPI can be configured to communicate that a shock will be delivered imminently.

The warning HPI can be distinct from the opening HPI. In particular, the indications can be different in content, in the way they are delivered, and/or in the meaning that they are designed to convey to the patient. For example, in some embodiments the opening HPI communicates to the patient that their WCD system has not made a determination yet, and it does not require the patient to do anything to avoid a shock. On the other hand, in many embodiments the warning HPI of operation 440 informs that a shock is imminent unless the patient does something, like enter a cancel input in the user interface.

According to an optional next operation 494, if a cancel input is received, execution may return to operation 410. In particular, the user interface can be configured to receive a cancel input. Even if the cardiac arrhythmia is so validated, the discharge circuit can be controlled to instead not deliver a shock responsive to the cardiac arrhythmia, if a cancel input is received by the user interface within a time window after the warning HPI of operation 440 is caused to be output.

Else, if at operation 494 a cancel input is not received then, according to another operation 499, the discharge circuit is instead controlled to deliver a shock, for example within 3 min from when the warning HPI was caused to be output for that event, and preferably before 3 min passes.

In FIG. 5, from box 525, if it is determined that the cardiac arrhythmia is so validated, a timeline 542 indicates that a warning HPI event 543 can take place, for example according to operation 440. In addition, timeline 598 indicates that a shock delivery event 599 may take place, while timeline 579 indicates that no closing HPI event takes place.

These embodiments that include an opening HPI can be combined with other embodiments. For example, from this document alone, these other embodiments include ones with a closing HPI, embodiments where there is confirmation of the cardiac arrhythmia in addition to validation, embodiments with shocking if the patient has VF but not necessarily if VT, a different delay or validation time for VT than for VF, a different HPI for VT than for VF, etc.

In some embodiments, a WCD system may output a closing human-perceptible indication ("HPI"), after detecting a shockable cardiac arrhythmia, and after further determining that it will not shock. The closing HPI may be associated with closing an event, such as when an event is closed in software, where a record is kept. Examples are now described.

Figure 6:
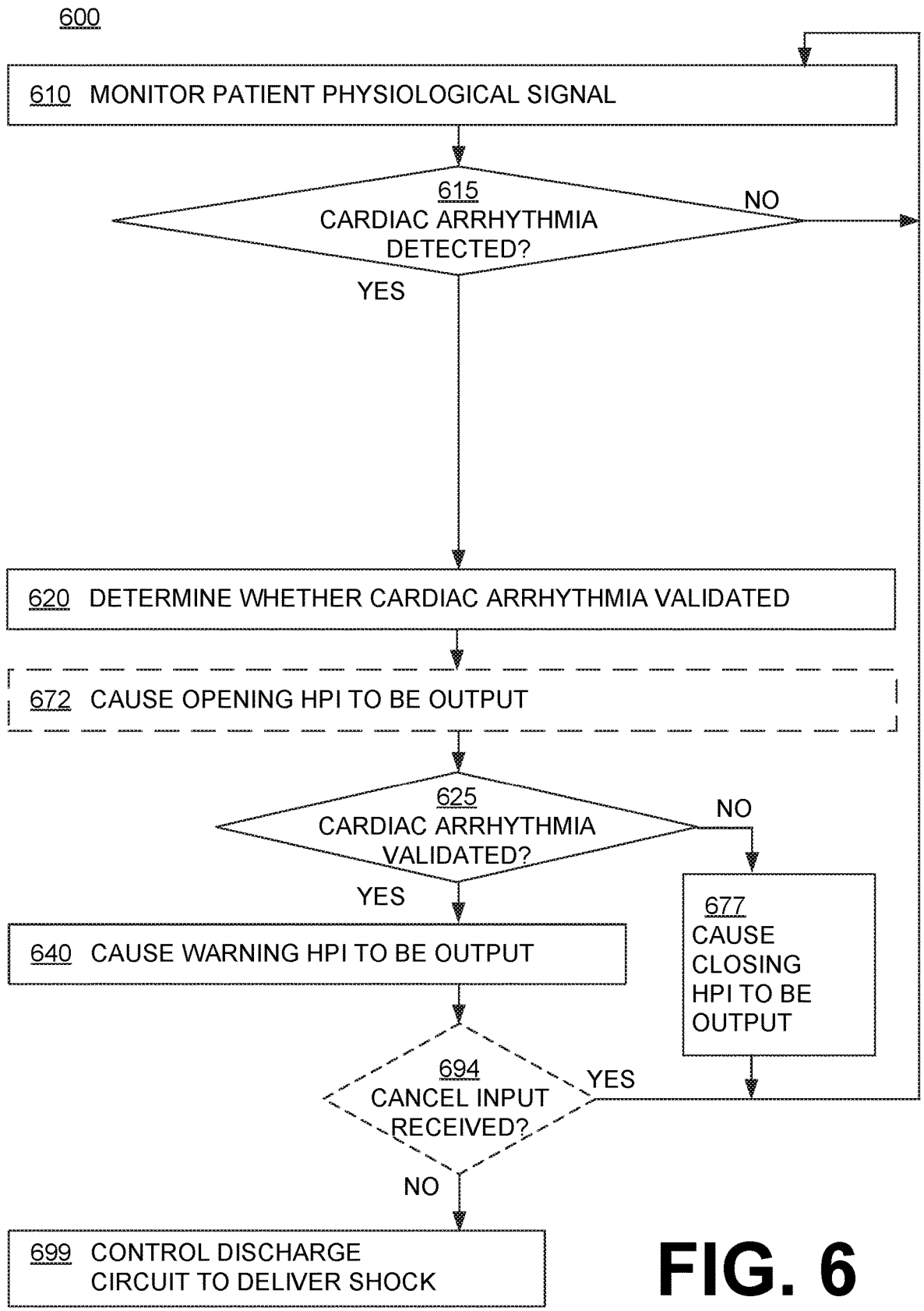
FIG. 6 is a flowchart for illustrating methods according to embodiments.

FIG. 6 shows a flowchart 600 for describing methods according to embodiments. Flowchart 600 has many elements that are similar to flowchart 400 of FIG. 4. In addition, the sample series of events of FIG. 5 may also result from methods of the flowchart of FIG. 6.

In FIG. 6, operations 610, 615, 620, 672, 625, 640 and 694 can be performed as described respectively for operations 410, 415, 420, 472, 425, 440, and 494 of FIG. 4. In other words, a shockable cardiac arrhythmia is detected, etc. Of those operations, at least operations 672 and 694 are optional.

If, at operation 625 it is determined that the cardiac arrhythmia is so validated then, according to an operation 699, the discharge circuit can be controlled to instead deliver a shock within some time from when it was determined that the cardiac arrhythmia is so validated. The shock can be delivered, for example within 2.5 min or less, for this event.

If, at operation 625 it is determined that the cardiac arrhythmia is not so validated, execution may return to operation 610 without shocking for this event. In addition, according to another operation 677, a closing HPI is caused to be output. The closing HPI can be configured to communicate to the patient that it was decided not to shock responsive to the cardiac arrhythmia, so the patient can relax and return to his or her other business. This may be communicated in a number of ways. In some embodiments, the closing HPI includes a voice message, which can say something like: "HAPPY THAT YOUR RHYTHM IS RESTORED, WILL NOT SHOCK THIS TIME". In alternate, and more discreet, embodiments the closing HPI includes one or more vibrations. For example, a group of consecutive vibrations may be used, which have progressively diminishing intensities. If, at operation 625 it is determined that the cardiac arrhythmia is not so validated, the discharge circuit can be further controlled to not deliver a shock for some time from when it was determined that the cardiac arrhythmia is not so validated, for example for at least 25 min. Of course, this time can become shorter if the patient has another event soon thereafter, and so on.

These embodiments that include a closing HPI can be combined with other embodiments. For example, from this document alone, these other embodiments include ones with an opening HPI, embodiments where there is confirmation of the cardiac arrhythmia in addition to validation, embodiments with shocking if the patient has VF but not necessarily if VT, a different delay or validation time for VT than for VF, a different HPI for VT than for VF, etc.

In some embodiments, a WCD system may first determine whether or not the cardiac arrhythmia is validated, for example according to a validation criterion. If so, the WCD system may further determine whether or not the cardiac arrhythmia is confirmed according to a confirmation criterion, and then shock or not shock accordingly. Examples are now described.

Figure 7:
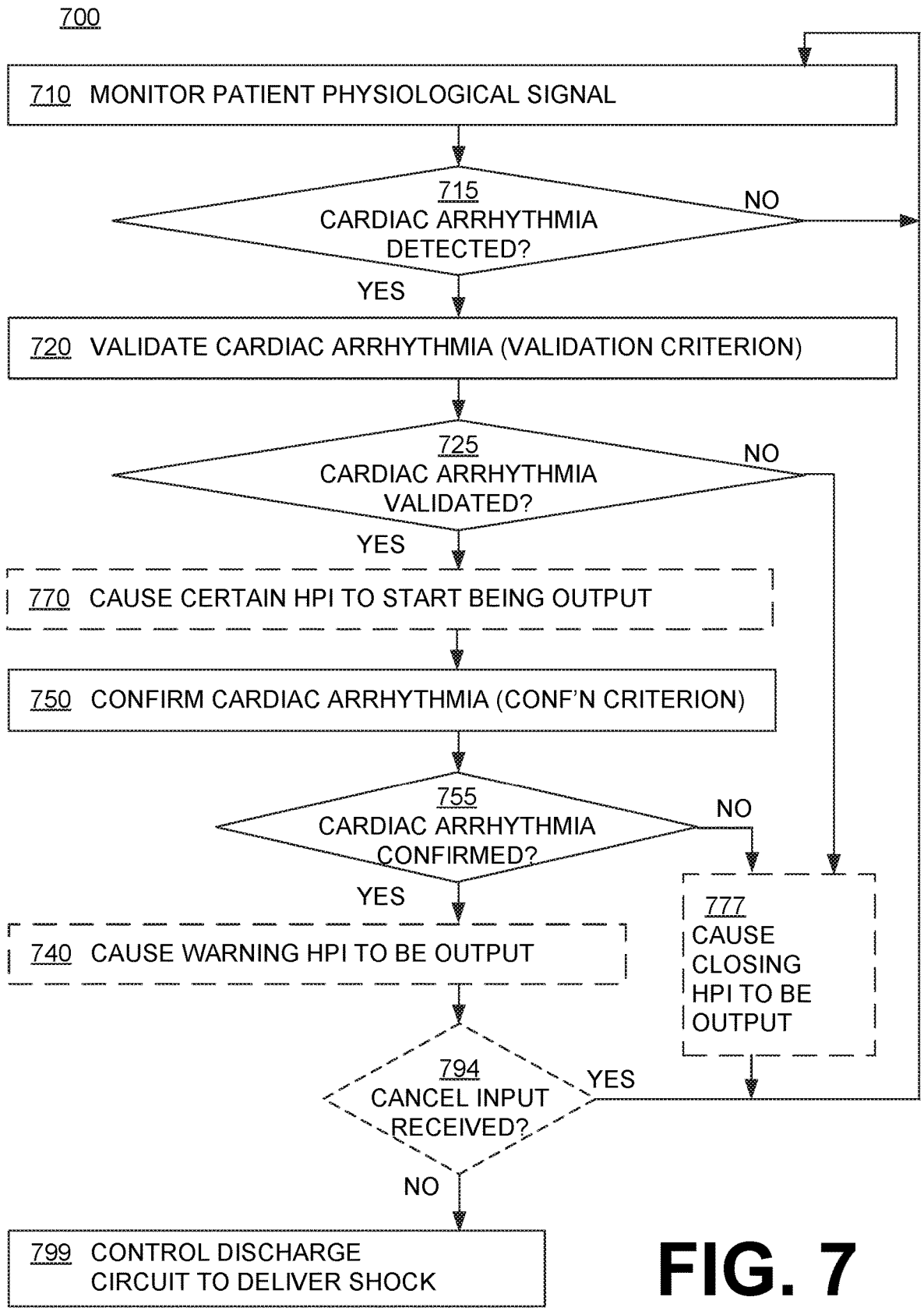
FIG. 7 is a flowchart for illustrating methods according to embodiments.
Figure 8:
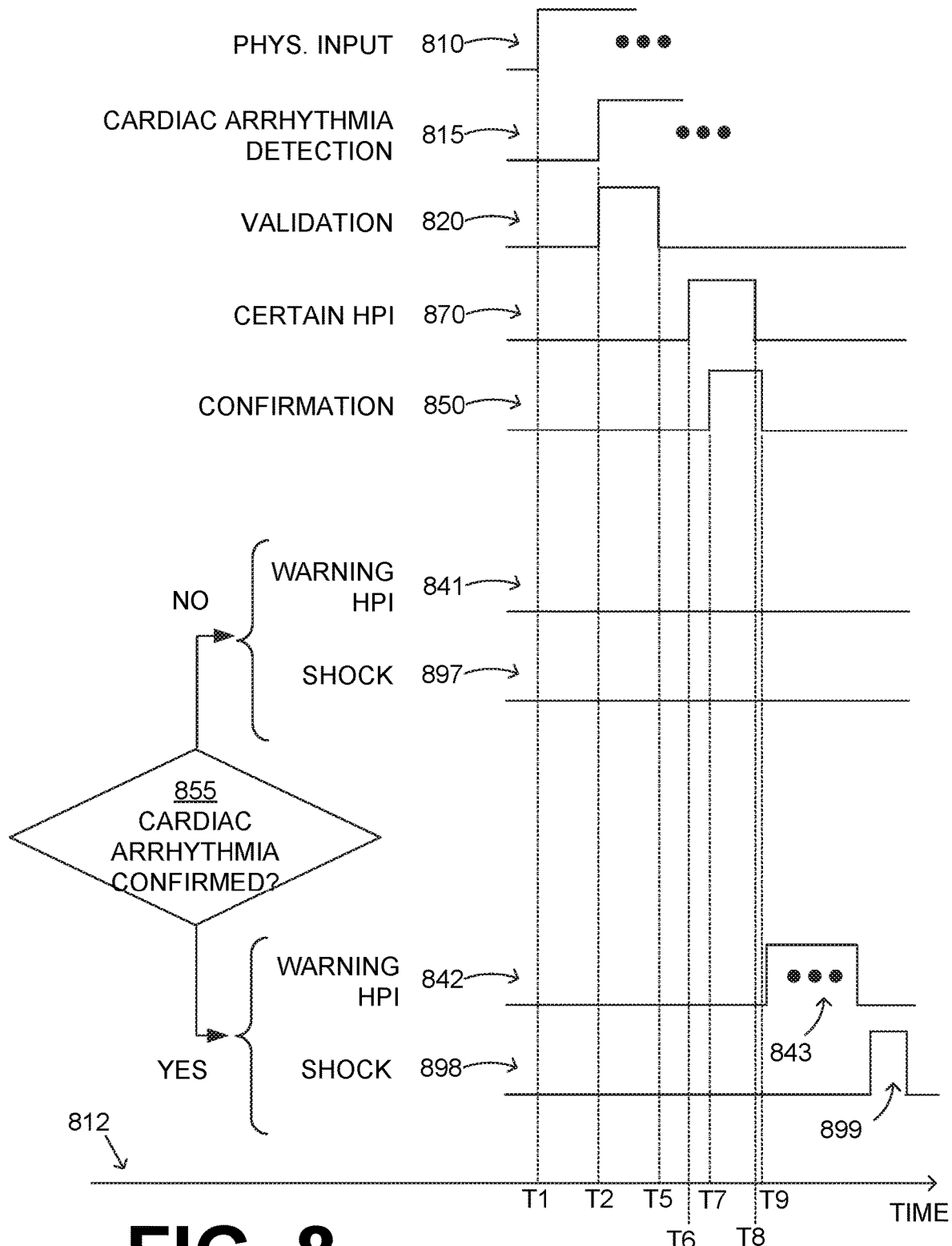
FIG. 8 is a time diagram of a sample series of events that may result from methods of the flowchart of FIG. 7.

FIG. 7 shows a flowchart 700 for describing methods according to embodiments. In addition, FIG. 8 is a time diagram of a sample series of events that may result from methods of the flowchart of FIG. 7. Of course, a different series of events may result from the methods of the flowchart of FIG. 7. The events of FIG. 8 are shown along a time axis 812, with intercepts that are not to scale. This portion of this description proceeds by referring to both diagrams.

In FIG. 7, operations 710, 715, 720, 725, 740, 794 and 777 can be performed as previously described for respectively operations 410, 415, 420, 425, 440, 494 and 677. In other words, a shockable cardiac arrhythmia is detected, etc. Of those operations, at least operations 740, 794 and 777 are optional. In FIG. 8, timelines 810, 815, 820 can be as described for timelines 510, 515 and 520. In addition, an opening HPI may be caused to be output as per the above, but such is not shown so as not to obscure the drawings.

If, at operation 725 it is determined that the detected cardiac arrhythmia is so validated then, according to another operation 770, a certain HPI can be caused to start being output. The certain HPI can accomplish a number of functions. One such function may be to inform the patient, who may be only tachycardic and thus conscious, that more analysis of their rhythm will be performed in the form of a confirmation. Again, this may give the patient the confidence that he or she will not be shocked unnecessarily, while they need not do anything to prevent a shock. After starting being output, the certain HPI of operation 770 can continue, to sustain the patient's confidence. For example, in FIG. 8, timeline 870 shows the certain HPI, which starts being output at time T6, and lasts until time T8.

Returning to FIG. 7, after operation 770, according to another operation 750 it can be further determined whether or not the cardiac arrhythmia is confirmed. In FIG. 8, the confirmation of operation 750 is shown by a timeline 850 as taking place between times T7 and T9. It will be appreciated that time T7 in this example is after time T6, which is when the certain HPI started being output.

The determination of operation 750 can be performed according to a confirmation criterion, meaning depending on whether or not the confirmation criterion is met. The confirmation criterion can be different from or the same as the validation criterion. In some embodiments, the validation criterion can include that the cardiac arrhythmia is maintained for a validation time, the confirmation criterion can include that the cardiac arrhythmia is maintained for a confirmation time, and the confirmation time can be the same or different from the validation time. In some embodiments, the confirmation time is longer than the validation time, which is why the certain HPI may help the patient with their comfort that their system is working.

Subsequent operations may depend on the determination of whether the cardiac arrhythmia is so confirmed or not. Where it is written in this document that it is determined that the cardiac arrhythmia is or is not so confirmed, it means to be or not be confirmed according to the previously mentioned confirmation criterion, the determination of such confirmation, etc.

According to another operation 755, if it is determined that the cardiac arrhythmia is not so confirmed, execution may return to operation 710, with optionally also executing operation 777 as mentioned above for operation 677. In such a case, there may be no shocking for this event in fact the discharge circuit can be controlled to not deliver a shock for some time, e.g. at least 22 min from when the cardiac arrhythmia is not so confirmed, because the patient may not need a shock for that time. Of course, this time can become shorter if the patient has another event soon thereafter, and so on.

If, at operation 755 it is determined that the cardiac arrhythmia is so confirmed then shocking may be needed for this event. Thus, according to an operation 799, the discharge circuit can be controlled to deliver a shock within some time from when it was determined that the cardiac arrhythmia is so confirmed, for example within 4.8 min or preferably less.

Similarly, referring to FIG. 8, from box 855, if it can be determined whether or not the cardiac arrhythmia is so confirmed. If not, then timelines 841 and 897 can be as timelines 541 and 597, respectively indicating no warning HPI and no shock. Else, if the cardiac arrhythmia is so confirmed, then timeline 842 indicates a warning HPI event 843, and timeline 898 indicates a shock delivery event 899.

These embodiments that include confirmation in addition to validation can be combined with other embodiments. For example, from this document alone, these other embodiments include ones with shocking if the patient has VF but not necessarily if VT, a different delay or validation time for VT than for VF, a different HPI for VT than for VF, etc.

In some embodiments, a WCD system may detect whether a cardiac arrhythmia is of a first type or of a second type. If the cardiac arrhythmia is of the first type, the WCD system may shock the patient anyway. If the cardiac arrhythmia is of the second type, however, the WCD system may determine whether or not the cardiac arrhythmia is confirmed, for example according to a confirmation criterion, and then shock or not shock accordingly. Examples are now described.

Figure 9:
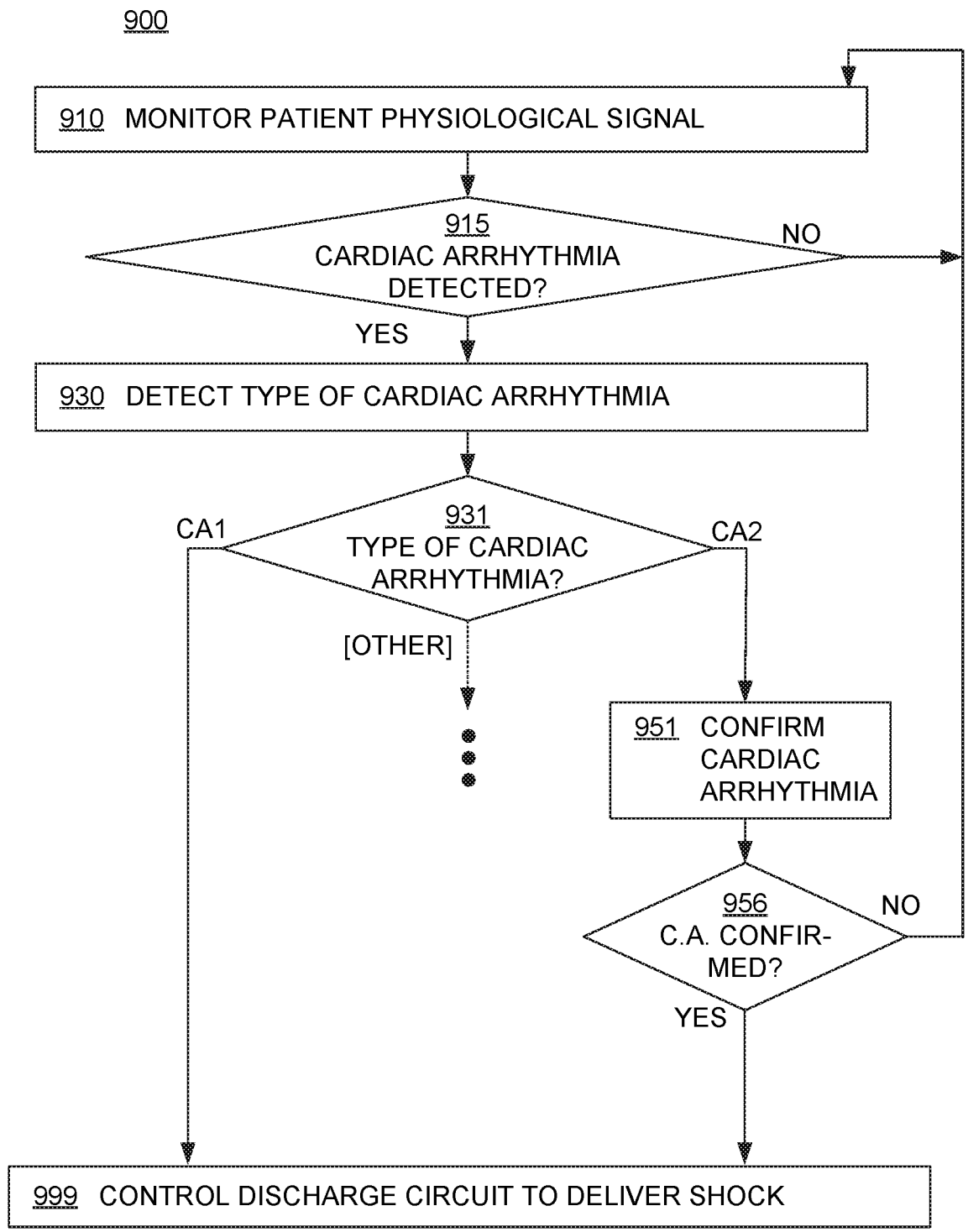
FIG. 9 is a flowchart for illustrating methods according to embodiments.

FIG. 9 shows a flowchart 900 for describing methods according to embodiments. In FIG. 9, operations 910 and 915 can be performed as described above for operations 410 and 415 respectively. In other words, a shockable cardiac arrhythmia is detected, etc. In addition, an opening HPI can optionally be caused to be output, for example prior to completing the determination of the type at operation 930 that is described later. Moreover, it may be optionally determined whether or not the cardiac arrhythmia is validated according to a validation criterion. In such embodiments, the opening HPI can be caused to be output prior to completing the determination of whether the cardiac arrhythmia is so validated. Subsequent actions, such as determining the type, validating, etc. may be performed responsive to determining that the cardiac arrhythmia is so validated.

If at operation 915 a cardiac arrhythmia is detected then, according to another operation 930, it may be determined whether a type of the cardiac arrhythmia is at least one of a first type ("CA1") and a second type ("CA2"). There can be two, three, or more possible such types. Embodiments may act differently, depending on the type determined at operation 930.

In some embodiments, the first type ("CA1") of detected cardiac arrhythmias includes Ventricular Fibrillation. In some embodiments, CA1 includes Ventricular Tachycardia, where a heart rate of the patient has a value larger than a first heart rate threshold. An example is now described.

Figure 10:
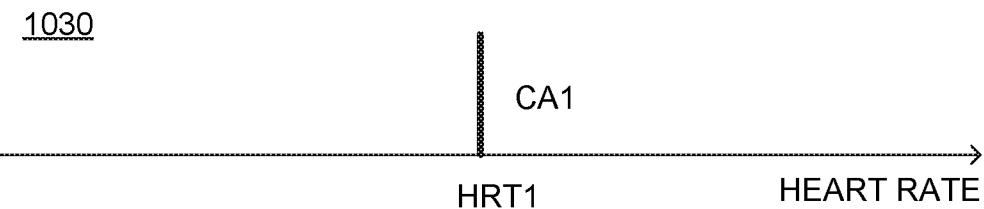
FIG. 10 is a diagram illustrating how it may be determined that a detected arrhythmia is of a first type according to embodiments.

FIG. 10 shows a diagram 1030, where detected cardiac arrhythmias may be plotted according to their heart rate. In diagram 1030 a HEART RATE axis has a first heart rate threshold HRT1. Suggested values for HRT1 are discussed below. The type of cardiac arrhythmias whose heart rate has a value larger than HRT1 can be determined to be CA1 The remaining cardiac arrhythmias can be determined to be either all of the same type (e.g. CA2), or further subdivided according to additional types, etc. It will be appreciated, then, that fast VT may be thus classified as type CA1, while slower VT otherwise.

In some embodiments, the second type ("CA2") of detected cardiac arrhythmias includes Ventricular Tachycardia, where a heart rate of the patient has a value less than a second heart rate threshold. An example is now described.

Figure 11:
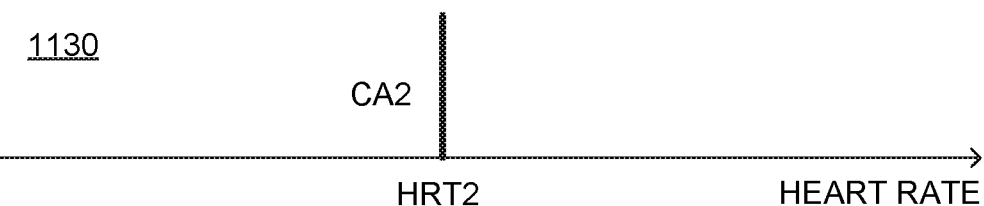
FIG. 11 is a diagram illustrating how it may be determined that a detected arrhythmia is of a second type according to embodiments.

FIG. 11 shows a diagram 1130, where detected cardiac arrhythmias may be plotted according to their heart rate. In diagram 1130 a HEART RATE axis has a second heart rate threshold HRT2. Suggested values for HRT1 are discussed below. The type of cardiac arrhythmias whose heart rate has a value less than HRT2 can be determined to be CA2. The remaining cardiac arrhythmias can be determined to be either all of the same type (e.g. CA1), or further subdivided according to additional types, etc. It will be appreciated, then, that slower VT may be thus classified as type CA2.

In some embodiments, if a value of the heart rate of the patient is within a range, the type is determined to be CA1 or CA2 depending both on the value of the heart rate and on a value of a width of detected QRS complexes of the patient. An example is now described.

Figure 12:
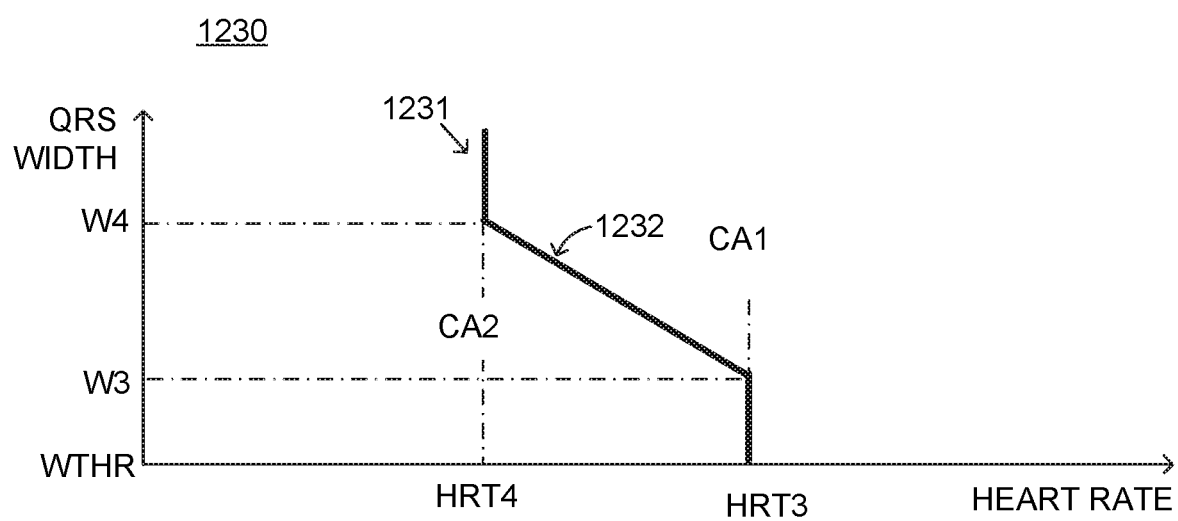
FIG. 12 is a diagram illustrating how it may be determined whether a detected arrhythmia is of a first type or of a second type according to embodiments.

FIG. 12 shows a diagram 1230, where detected cardiac arrhythmias may be plotted according to both their heart rate and the width of QRS complexes, based on orthogonal axes. The horizontal axis is for the heart rate. The vertical axis is for the QRS width, which can be measured by the algorithm at the base of the QRS complex. It will be noted that the vertical axis starts at a minimum threshold value WTHR. Above that value, QRS complexes start deteriorating. Below that value, it is possible that no shock is advised. A good value for WTHR can be about 80 msec.

In diagram 1230 a broken line 1231 divides the space in two sectors or zones, one for CA1 and one for CA2. At least the type of cardiac arrhythmias whose heart rate has a value larger than HRT3 can be determined to be CA1, and at least the type of cardiac arrhythmias whose heart rate has a value less than HRT4 can be determined to be CA2. In addition, if the value of the heart rate is within the range of HRT4 and HRT3, then the type can be determined depending both on the value of the heart rate on the horizontal axis and on a value of a width of detected QRS complexes on the vertical axis. The determination takes place from line segment 1232 of broken line 1231.

A good value for HRT4 is 170 bpm (beats per minute). A good value for HRT3 is 200 bpm. A good value for W3 is 120 msec, and for W4 is 150 msec. Once values for these parameters are determined, then an equation can be constructed for line segment 1232 using analytic geometry, for a processor to use.

In the example of FIG. 12, broken line 1231 has only linear segments, but that is only an example. Linear segments are preferred, because the computation for the determination of operation 930 is easier, as seen for line segment 1232.

Where performing such computations based on the QRS width would be too taxing on resources, and where only two types need be determined, then FIGS. 10 and 11 may be used in a combined form. In such a case, HRT1 can be set equal to HRT2, and both can have a value between the proposed values of HRT3 and HRT4, such as 200 bpm. In other words, the heart rhythms can be separated according to a certain heart rate threshold: CA1 may include a rhythm where a heart rate of the patient has a value less than the certain heart rate threshold, while CA2 may include a rhythm where the heart rate has a value larger than the certain heart rate threshold. The certain heart rate threshold can be, for example 200 bpm; a rate higher than that can be designated as the VF zone, while a rate of 170-200 bpm can be designated as the VT zone.

In some embodiments, there are two types of cardiac arrhythmias: shockable VF/shockable VT. In addition to the heart rate and the QRS width, one may further incorporate another attribute called QRS organization. QRS organization might be assessed by cross-correlating detected QRS complexes. Rhythms in which the QRS complexes show a high correlation would be said to be relatively "organized," while rhythms with a low correlation would be "disorganized."

Accordingly, there may be no shock while the heart rate is <150 bpm and the QRS width <120 msec. At least monomorphic VT may be identified as a heart rate >150 bpm, QRS width >120 msec, and high QRS organization. VF may be identified as a heart rate is >200 bpm, QRS width >120 msec, and low QRS organization.

In some embodiments where the physiological signal is an ECG waveform, the distinction between CA1 and CA2 is based on an amplitude of an ECG waveform. A type of a cardiac arrhythmia can be CA1 if its ECG waveform has an amplitude smaller than a threshold amplitude, and CA2 if its ECG waveform has an amplitude larger than the threshold amplitude. The threshold amplitude can be a suitable value, for example 200 µV.

Returning to FIG. 9, according to another operation 931, it is inquired which was the type of the detected cardiac arrhythmia determined at operation 930. In the examples of this document, cardiac arrhythmias whose type is CA1 are deemed more severe than otherwise, e.g. those whose type is CA2. Operation 931 anticipates that there could be two or even more types. For example, another type can be Atrial Fibrillation ("AF").

In some embodiments, if at operation 931 it is determined that the type is CA1 then, according to an operation 999, the discharge circuit can be controlled to deliver a shock within sometime of determining the type, for example within 2.9 min and preferably less than that.

In some embodiments, if at operation 931 it is determined that the type is CA2 then, according to another operation 951, it can be further determined whether or not the cardiac arrhythmia is confirmed. This confirmation can be performed in a number of ways, as will be seen later in this document.

According to one more operation 956, if the cardiac arrhythmia is so confirmed at operation 951, then the discharge circuit can be controlled to deliver a shock according to operation 999. Operation 999 may be thus performed within some time from when the cardiac arrhythmia is so confirmed at operation 951, for example within 4.8 min. But if the cardiac arrhythmia is not so confirmed at operation 951, then execution may return to operation 910, and the discharge circuit can be controlled to not deliver a shock for some time. This time can be, for example at least 24 min from when the cardiac arrhythmia is not so confirmed at operation 951. In addition, a closing HPI may be caused to be output responsive to the cardiac arrhythmia not being so confirmed, in conjunction with returning to operation 910.

Operation 951 may be performed in a number of ways. It should be kept in mind that, in many embodiments, the detected cardiac arrhythmia at this time is known to be of the second type, which will hopefully self-terminate without needing to administer a shock. Examples are now described.

In some embodiments, it is determined whether or not the cardiac arrhythmia is confirmed according to a confirmation criterion. In some embodiments, the confirmation criterion includes that the cardiac arrhythmia is maintained for a confirmation time. In some embodiments, the confirmation criterion includes that a heart rate of the patient increases during a confirmation time. Additional embodiments are now described.

Figure 13:
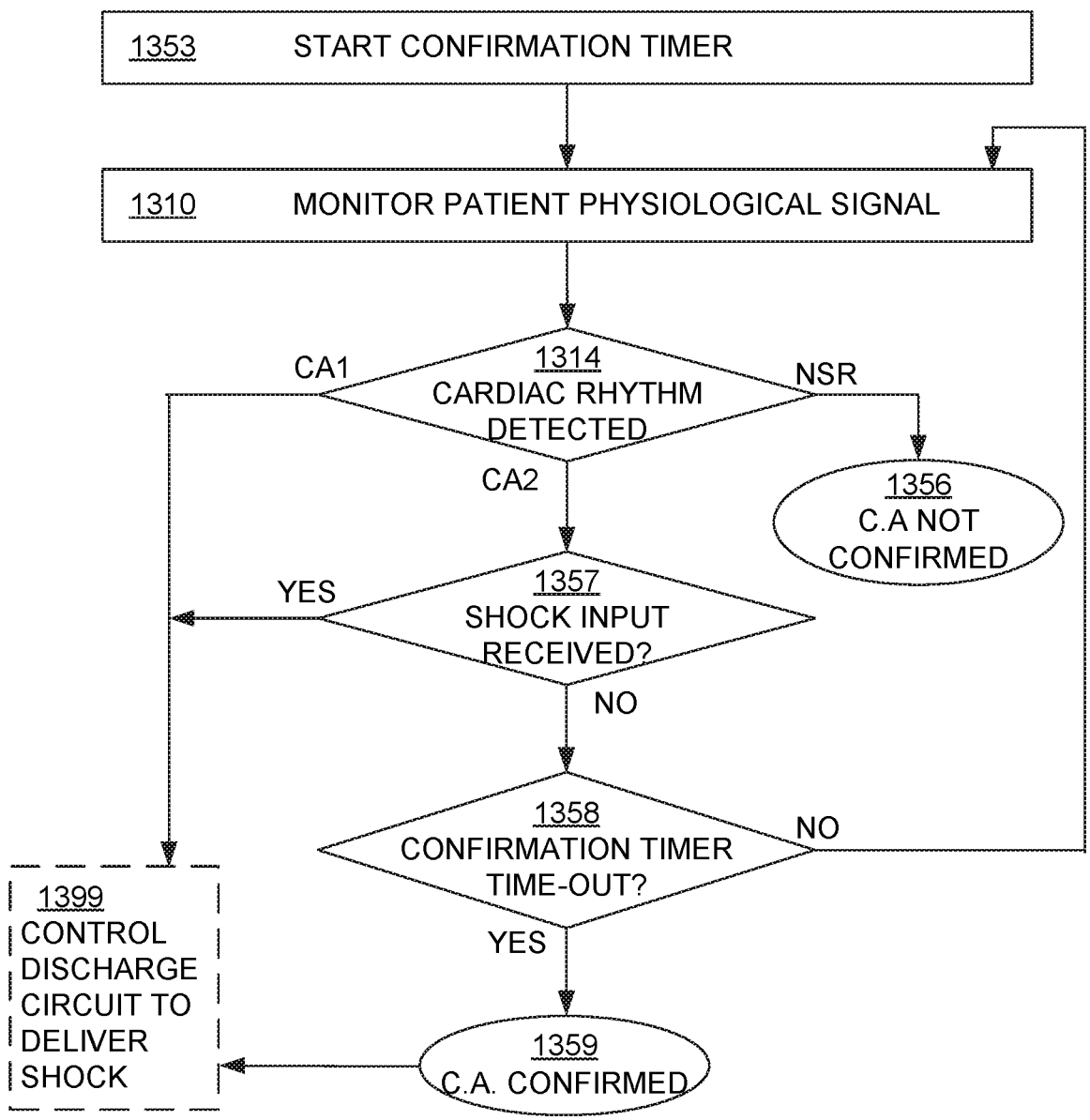
FIG. 13 is a flowchart for illustrating methods of how a cardiac arrhythmia may be confirmed according to embodiments.

FIG. 13 shows a flowchart 1351 for describing methods according to embodiments. Some of these methods may be applied to flowchart 900, or others where a detected cardiac arrhythmia is being confirmed.

According to an operation 1353, a confirmation timer may be started. According to another operation 1310, a patient physiological signal may be monitored. At this point, if flowchart 1351 is applied to flowchart 900, the patient physiological signal may help detect a cardiac arrhythmia of the second type ("CA2").

According to another operation 1314, it is inquired what cardiac rhythm is being detected. If the rhythm is a normal sinus rhythm (NSR), it may be that the heart rhythm has been restored by itself. Then, according to a state 1356, the cardiac arrhythmia is not confirmed. If flowchart 1351 is being applied to flowchart 900, execution then returns to operation 910.

If at operation 1314 of FIG. 13 the cardiac arrhythmia is of the first type ("CA1"), such as VF or fast VT, execution may proceed to operation 1399. The latter may be performed as operation 999 in flowchart 900.

If at operation 1314 of FIG. 13 the cardiac arrhythmia is still of the second type ("CA2"), it may be that the patient has been experiencing VT. The above described option of checking as to whether the heart rate has been increasing persistently may be checked at this time.

At this stage, the patient may have become very uncomfortable with their cardiac rhythm, in fact so uncomfortable that the patient may prefer to be shocked over waiting for the arrhythmia to self-terminate. In some embodiments of a WCD system, the user interface is further configured to receive a shock input by the patient, such as by the patient pushing a button titled: "SHOCK ME NOW". According to another operation 1357, if such a shock input is received, execution may proceed to operation 1399. In other words, in such embodiments, if the type has been determined to be CA2, the discharge circuit can be controlled to deliver a shock responsive to the received shock input. Operation 1399 can be performed within sometime after receiving the shock input, for example within 1.6 min of receiving the shock input.

If at operation 1357 no shock input has been received, then according to another operation 1358 it is inquired whether the confirmation timer that started at operation 1353 has timed out. If not, execution may return to operation 1310. If yes then, according to a state 1359, the cardiac arrhythmia is confirmed, and execution may proceed to operation 1399.

These embodiments that shock a patient with VF but not necessarily with VT can be combined with other embodiments. For example, from this document alone, these other embodiments include ones with a different delay or validation time for VT than for VF, a different HPI for VT than for VF, etc.

In some embodiments, a WCD system may detect whether a cardiac arrhythmia is of a first type or of a second type. The WCD system may validate the detected cardiac arrhythmia, and output an HPI with a different delay, depending on the type. Examples are now described.

Figure 14:
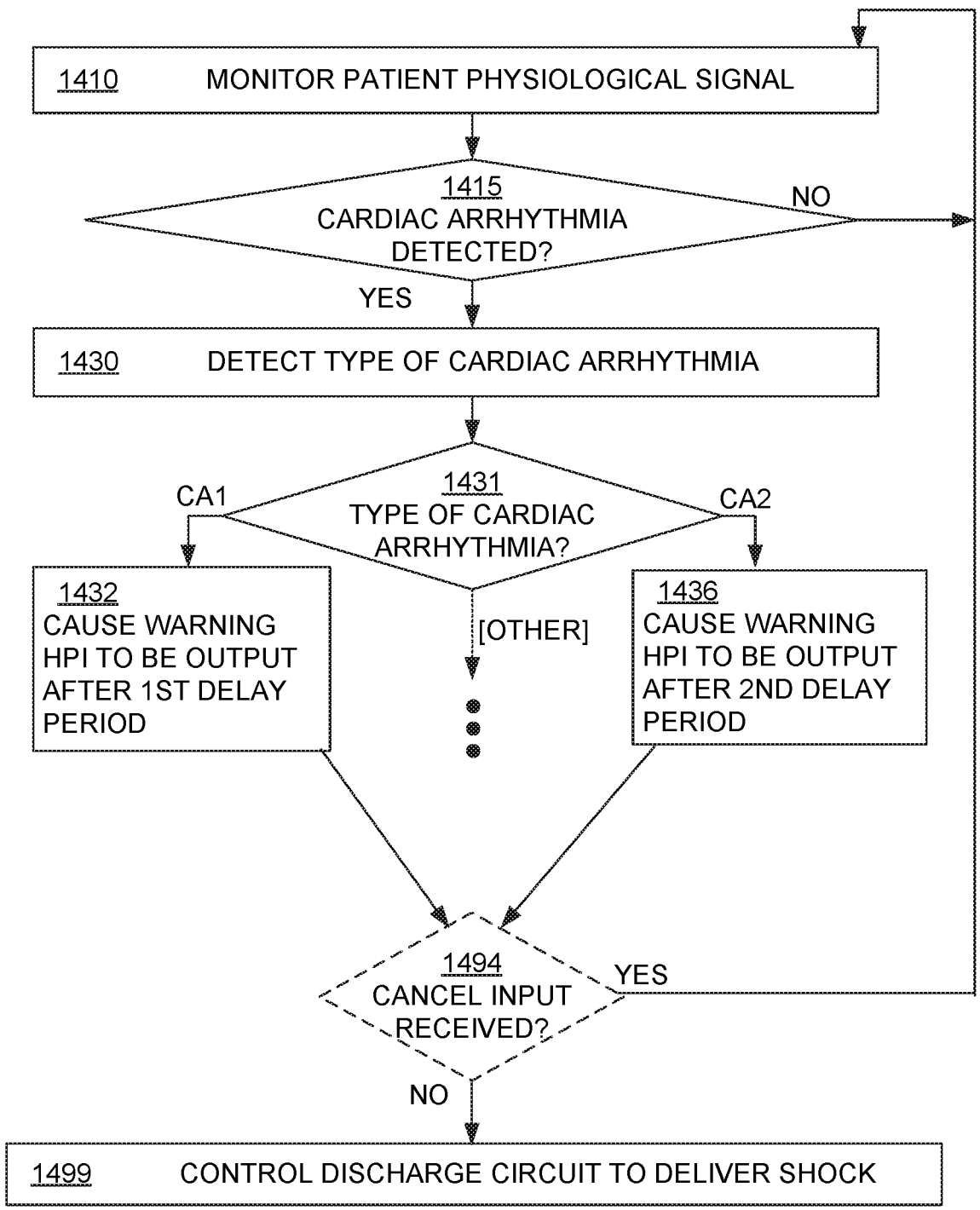
FIG. 14 is a flowchart for illustrating methods according to embodiments.
Figure 15:
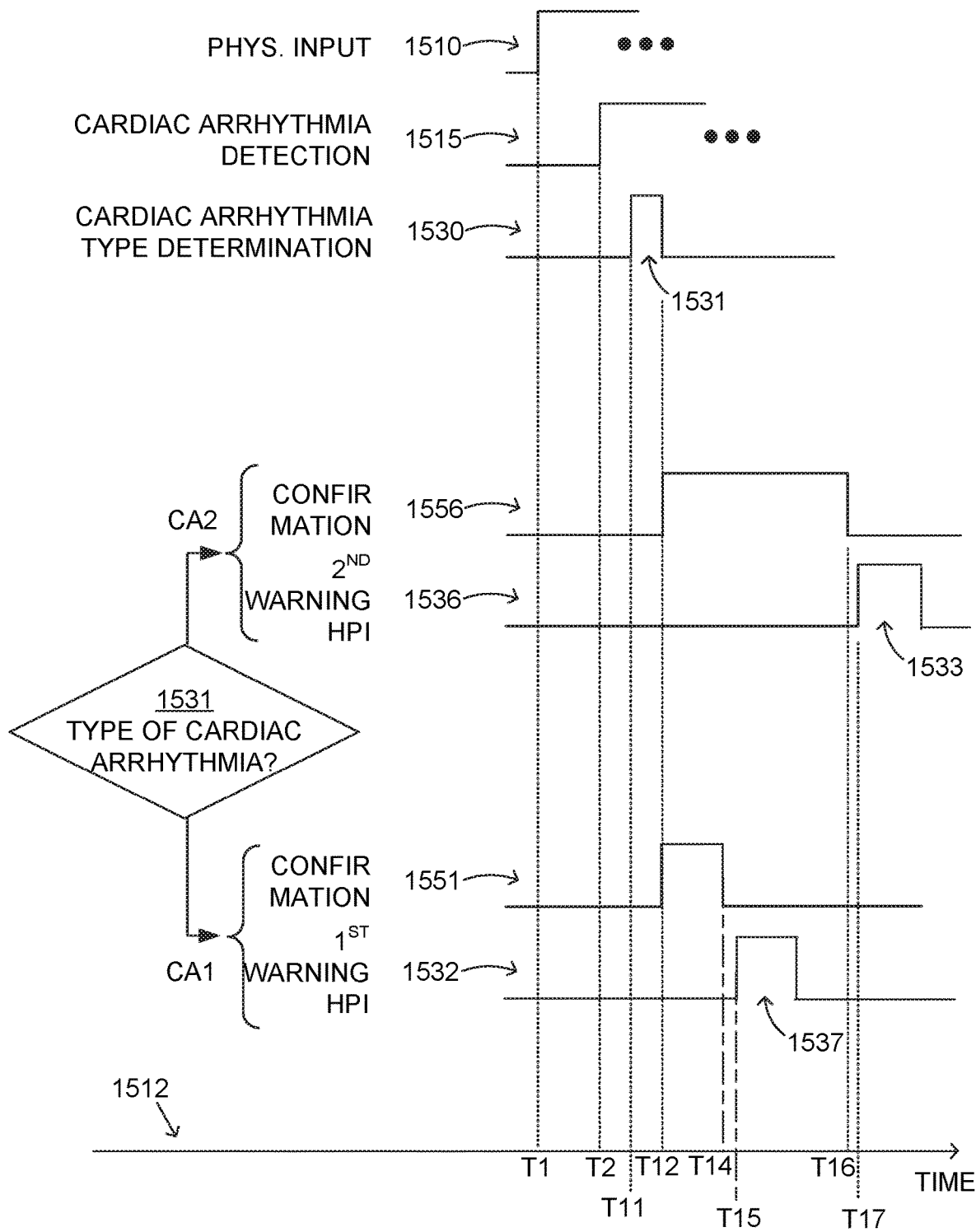
FIG. 15 is a time diagram of a sample series of events that may result from methods of the flowchart of FIG. 14.

FIG. 14 shows a flowchart 1400 for describing methods according to embodiments. In addition, FIG. 15 is a time diagram of a sample series of events that may result from methods of the flowchart of FIG. 14. Of course, a different series of events may result from the methods of the flowchart of FIG. 14. The events of FIG. 15 are shown along a time axis 1512, with intercepts that are not to scale. This portion of this description proceeds by referring to both diagrams.

In FIG. 14, operations 1410, 1415, 1430 and 1431 can be performed as described above for respective operations 410, 415, 930 and 931. In other words, a shockable cardiac arrhythmia is detected, its type is determined, etc.

In parallel referring to FIG. 15, timelines 1510 and 1515 can be as described for timelines 510 and 515. Moreover, timeline 1530 shows a type determination event 1531 of performing operation 1430, which starts at time T11 and ends at time T12.

In addition, although not shown in flowchart 1400 or in FIG. 15, in some embodiments an opening HPI is caused to be output responsive to detecting the cardiac arrhythmia, prior to completing the determination of the type. Moreover, the cardiac arrhythmia may be validated according to a validation criterion, and the opening HPI can be caused to be output prior to completing the determination of whether the cardiac arrhythmia is so validated. In some embodiments, type determination event 1531 is performed quickly and easily during such a validation, and thus it does not delay other actions.

If at operation 1431 it is determined that the type is CA1 then, according to another operation 1432, a first warning HPI is caused to be output. Operation 1432 may be performed after a first delay period elapses, since the type is determined at operation 1430.

If at operation 1431 it is determined that the type is CA2 then, according to another operation 1436, a second warning HPI is caused to be output. The first warning HPI can be the same or different than the second warning HPI. It is preferred that they are the same, for the patient to not have to be trained to many different commands.

Operation 1436 may be performed after a second delay period elapses, since the type is determined at operation 1430. The second delay period may have a duration at least 20% different from a duration of the first delay period. For example, the first delay period could be up to 10 sec, or even 20 sec. On the other hand, the second delay period can have a duration of at least 25 sec, and even 45 sec, both for better analysis and also in order to give a VT the opportunity to self-terminate. In embodiments, these delay periods are programmable.

After operation 1432 or 1436, according to an operation 1499, the discharge circuit can be controlled to deliver a shock responsive to the cardiac arrhythmia. In some embodiments, this shock is canceled if, according to an operation 1494, a cancel input is received within a time window. In other words, the discharge circuit can be controlled to instead not deliver a shock responsive to the cardiac arrhythmia and bypass operation 1499, if a cancel input is received by the user interface within a time window after the first warning HPI or the second warning HPI is caused to be output.

In FIG. 15, box 1531 replicates the decision of box 1431. In some embodiments, if the type is CA1, it may be determined during the first delay period whether the cardiac arrhythmia is confirmed according to a CA1 confirmation criterion. The CA1 confirmation criterion could be that the cardiac arrhythmia is maintained for a CA1 confirmation time. Timeline 1551 shows the confirmation, where the CA1 confirmation time lasts between T12 and T14. The CA1 confirmation time may be, for example 10 sec if CA1 includes VF. Timeline 1532 then shows the first warning HPI event 1537 that starts at a later time T15.

In such embodiments, if the type is CA2, it may be determined during the second delay period whether the cardiac arrhythmia is confirmed according to a CA2 confirmation criterion. The CA2 confirmation criterion could be that the cardiac arrhythmia is maintained for a CA2 confirmation time. Timeline 1556 shows this confirmation, where the CA2 confirmation time lasts between T12 and T16. Timeline 1536 then shows the second warning HPI event 1533 that starts at a later time T17. In this example, the CA2 confirmation time has a duration at least 20% different from a duration of the CA1 confirmation time. The CA2 confirmation time may be, for example 45 sec if CA2 includes VT. The differences in the confirmation times may account for the differences in the respective delay periods.

FIG. 15 does not show the shock event that may follow the warning HPIs. This was done only not to clutter FIG. 15.

These embodiments that have a different delay or validation time for VT than for VF can be combined with other embodiments. For example, from this document alone, these other embodiments include ones with a different HPI for VT than for VF, etc.

In some embodiments, a WCD system may detect whether a cardiac arrhythmia is of a first type or of a second type. The WCD system may output different HPIs for the first type than the second type. Examples are now described.

Figure 16:
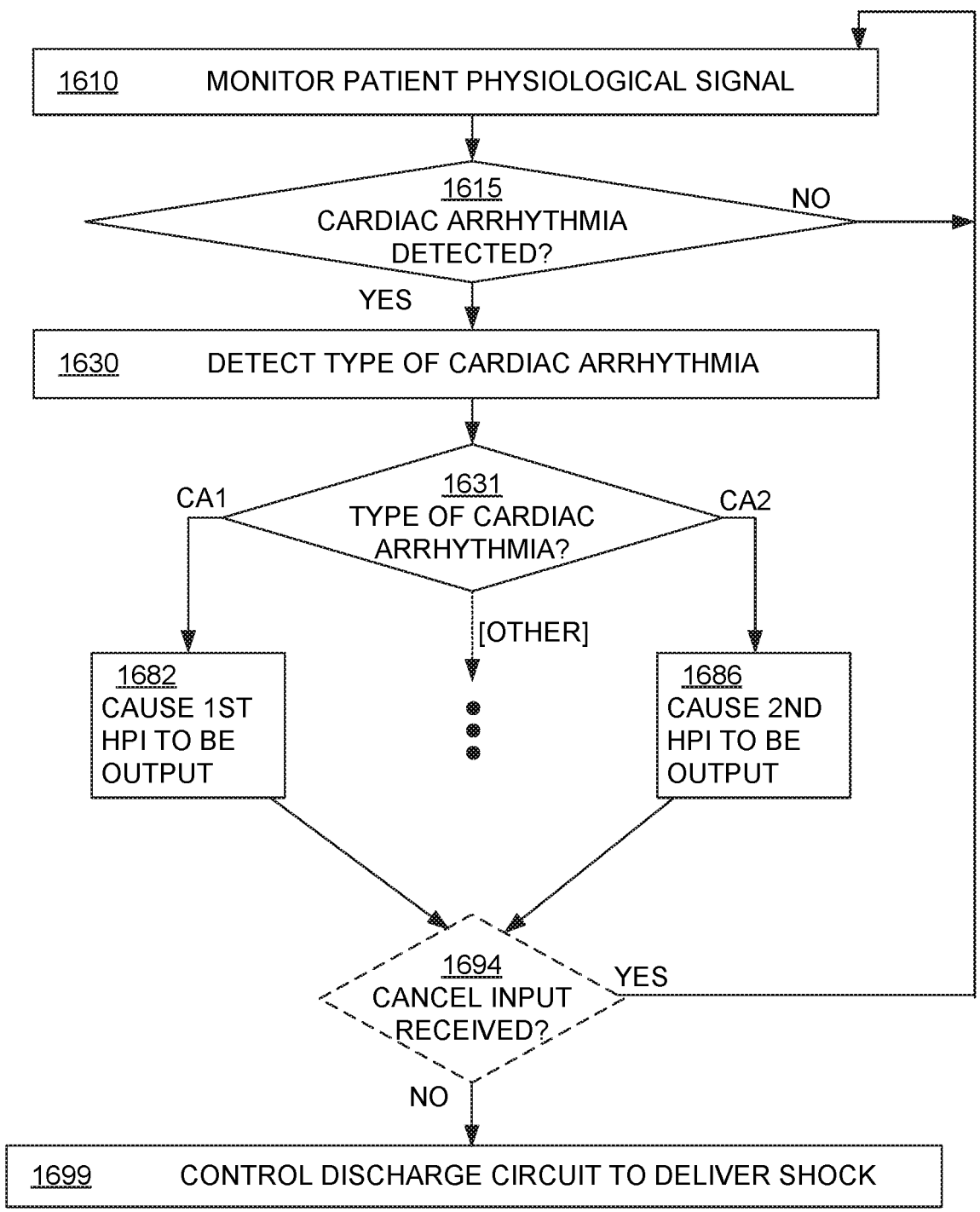
FIG. 16 is a flowchart for illustrating methods according to embodiments.

FIG. 16 shows a flowchart 1600 for describing methods according to embodiments. In FIG. 16, operations 1610, 1615, 1630, 1631, 1694 and 1699 can be performed as described above for respective operations 1410, 1415, 1430, 1431, 1494 and 1499. In other words, a shockable cardiac arrhythmia is detected, its type is determined, etc.

In addition, although not shown in flowchart 1600, in some embodiments an opening HPI is caused to be output responsive to detecting the cardiac arrhythmia, prior to completing the determination of the type. Moreover, the cardiac arrhythmia may be validated according to a validation criterion, and the opening HPI can be caused to be output prior to completing the determination of whether the cardiac arrhythmia is so validated.

If at operation 1631 it is determined that the type is CA1 then, according to another operation 1682, a first HPI is caused to be output. Else, if the type is CA2, according to another operation 1686 a second HPI is caused to be output.

The first HPI can be different from the second HPI for a number of reasons. For instance, the first HPI can be a warning HPI as described above, in which case entering a cancel input will avert a shock. On the other hand, the second HPI can be an HPI where the patient is informed that their rhythm is still being analyzed, whether that means being validated or confirmed.

The first HPI can be different from the second HPI in a number of ways. Examples are now described.

In some embodiments, the user interface includes at least a first and a second output device. The HPIs can come from different devices, in other words the first HPI can be output by the first output device, while the second HPI can be output by the second output device.

In some embodiments, the first and the second HPI can be from the same device. Examples are now described.

In some embodiments, the user interface includes a screen, but the displayed images are different. In other words, the first HPI can be a first image displayed by the screen, while the second HPI can be a second image displayed by the screen, which is different than the first image.

In some embodiments, the user interface includes a speaker that can play one or more audible sounds, but the sound messages are different. In other words, the first HPI can be a first sound message output by the speaker, while the second HPI can be a second sound message output by the speaker, which is different from the first sound message.

In some embodiments, the user interface includes an output device that can cause an HPI to be output at different intensity levels, be that louder for sound, brighter for light, more intense for vibration, and so on. The first HPI can be output by the output device at a first intensity level, while the second HPI can be output by the output device at a second intensity level, which is at least 20% different than the first intensity level. The intensity level may be measured by energy to actuate the device, perceived intensity by the user, etc.

In the methods described above, each operation can be performed as an affirmative step of doing, or causing to happen, what is written that can take place. Such doing or causing to happen can be by the whole system or device, or just one or more components of it. It will be recognized that the methods and the operations may be implemented in a number of ways, including using systems, devices and implementations described above. In addition, the order of operations is not constrained to what is shown, and different orders may be possible according to different embodiments. Examples of such alternate orderings may include overlapping, interleaved, interrupted, reordered, incremental, preparatory, supplemental, simultaneous, reverse, or other variant orderings, unless context dictates otherwise. Moreover, in certain embodiments, new operations may be added, or individual operations may be modified or deleted. The added operations can be, for example, from what is mentioned while primarily describing a different system, apparatus, device or method.

A person skilled in the art will be able to practice the present invention in view of this description, which is to be taken as a whole. Details have been included to provide a thorough understanding. In other instances, well-known aspects have not been described, in order to not obscure unnecessarily this description. Plus, any reference to any prior art in this description is not, and should not be taken as, an acknowledgement or any form of suggestion that such prior art forms parts of the common general knowledge in any country or any art.

This description includes one or more examples, but this fact does not limit how the invention may be practiced. Indeed, examples, instances, versions or embodiments of the invention may be practiced according to what is described, or yet differently, and also in conjunction with other present or future technologies. Other such embodiments include combinations and sub-combinations of features described herein, including for example, embodiments that are equivalent to the following: providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, while providing the features incorporated in such combinations and sub-combinations.

In this document, the phrases "constructed to" and/or "configured to" denote one or more actual states of construction and/or configuration that is fundamentally tied to physical characteristics of the element or feature preceding these phrases and, as such, reach well beyond merely describing an intended use. Any such elements or features can be implemented in a number of ways, as will be apparent to a person skilled in the art after reviewing the present disclosure, beyond any examples shown in this document.

Any and all parent, grandparent, great-grandparent, etc. patent applications, whether mentioned in this document or in an Application Data Sheet ("ADS") of this patent application, are hereby incorporated by reference herein as originally disclosed, including any priority claims made in those applications and any material incorporated by reference, to the extent such subject matter is not inconsistent herewith.

In this description a single reference numeral may be used consistently to denote a single item, aspect, component, or process. Moreover, a further effort may have been made in the drafting of this description to use similar though not identical reference numerals to denote other versions or embodiments of an item, aspect, component or process that are identical or at least similar or related. Where made, such a further effort was not required, but was nevertheless made gratuitously so as to accelerate comprehension by the reader. Even where made in this document, such a further effort might not have been made completely consistently for all of the versions or embodiments that are made possible by this description. Accordingly, the description controls in defining an item, aspect, component or process, rather than its reference numeral. Any similarity in reference numerals may be used to infer a similarity in the text, but not to confuse aspects where the text or other context indicates otherwise.

The claims of this document define certain combinations and subcombinations of elements, features and steps or operations, which are regarded as novel and non-obvious. Additional claims for other such combinations and subcombinations may be presented in this or a related document. These claims are intended to encompass within their scope all changes and modifications that are within the true spirit and scope of the subject matter described herein. The terms used herein, including in the claims, are generally intended as "open" terms. For example, the term "including" should be interpreted as "including but not limited to," the term "having" should be interpreted as "having at least," etc. If a specific number is ascribed to a claim recitation, this number is a minimum but not a maximum unless stated otherwise. For example, where a claim recites "a" component or "an" item, it means that it can have one or more of this component or item.

What is claimed is:

1. A wearable cardioverter defibrillator ("WCD") system, comprising:
    a support structure configured to be worn by a patient;
    a power source;
    an energy storage module configured to be coupled to the support structure, to be charged from the power source and to store an electrical charge;
    a discharge circuit coupled to the energy storage module, the discharge circuit controllable to discharge the electrical charge so as to cause a shock to be delivered to the patient;
    a measurement circuit configured to render a physiological input from a patient physiological signal;
    a user interface configured to output one or more human-perceptible indications; and
    a processor configured to:
        detect a cardiac arrhythmia of the patient from the physiological input;
        determine whether a type of the cardiac arrhythmia is at least one of a first type ("CA1") and a second type ("CA2");
        if the type is CA1, cause a first human-perceptible indication to be output, else if the type is CA2, cause a second human-perceptible indication to be output, the second human-perceptible indication being different from the first human-perceptible indication, wherein the first human-perceptible indication indicates that a shock is about to be delivered, and the second human-perceptible indication indicates that a confirmation process has been started; and
        then control the discharge circuit to deliver a shock responsive to the cardiac arrhythmia.

2. The WCD system of claim 1, in which CA1 includes Ventricular Fibrillation.

3. The WCD system of claim 1, in which CA1 includes Ventricular Tachycardia, where a heart rate of the patient has a value larger than a first heart rate threshold.

4. The WCD system of claim 1, in which the physiological signal includes an ECG waveform, and a type of a cardiac arrhythmia is CA1 if its ECG waveform has an amplitude smaller than a threshold amplitude.

5. The WCD system of claim 1, in which CA2 includes Ventricular Tachycardia, where a heart rate of the patient has a value less than a second heart rate threshold.

6. The WCD system of claim 1, in which if a value of the heart rate of the patient is within a range, the type is determined to be CA1 or CA2 depending both on the value of the heart rate and on a value of a width of detected QRS complexes of the patient.

7. The WCD system of claim 1, in which the physiological signal includes an ECG waveform, and a type of a cardiac arrhythmia is CA2 if its ECG waveform has an amplitude larger than a threshold amplitude.

8. The WCD system of claim 1, in which the processor is further configured to:
    cause an opening human-perceptible indication to be output responsive to detecting the cardiac arrhythmia, prior to completing the determination of the type.

9. The WCD system of claim 8, in which the processor is further configured to: determine whether or not the cardiac arrhythmia is validated according to a validation criterion, and
the opening human-perceptible indication is caused to be output prior to completing the determination of whether the cardiac arrhythmia is so validated.

10. The WCD system of claim 1, in which the user interface includes a first and a second output devices,
the first human-perceptible indication is output by the first output device, and
the second human-perceptible indication is output by the second output device.

11. The WCD system of claim 1, in which the user interface includes a screen,
the first human-perceptible indication is a first image displayed by the screen, and
the second human-perceptible indication is a second image displayed by the screen that is different than the first image.

12. The WCD system of claim 1, in which the user interface includes a speaker,
the first human-perceptible indication is a first sound message output by the speaker, and
the second human-perceptible indication is a second sound message output by the speaker that is different from the first sound message.

13. The WCD system of claim 1, in which the user interface includes an output device that can cause a human-perceptible indication to be output at different intensity levels,
the first human-perceptible indication is output by the output device at a first intensity level, and the second human-perceptible indication is output by the output device at a second intensity level that is different than the first intensity level by at least 20%.

14. A non-transitory computer-readable storage medium storing one or more programs which, when executed by at least one processor of a wearable cardioverter defibrillator ("WCD") system, the WCD comprising a support structure configured to be worn by a patient, a power source, an energy storage module configured to be coupled to the support structure and to be charged from the power source and to store an electrical charge, a discharge circuit controllable to discharge the electrical charge so as to cause a shock to be delivered to the patient, a measurement circuit rendering a physiological input from a patient physiological signal, a user interface and a processor, these one or more programs result in operations comprising:

detecting a cardiac arrhythmia of the patient from the physiological input;

determining whether a type of the cardiac arrhythmia is at least one of a first type ("CA1") and a second type ("CA2");

if the type is CA1, causing a first human-perceptible indication to be output, else if the type is CA2, causing a second human-perceptible indication to be output, the second human-perceptible indication being different from the first human-perceptible indication, wherein the first human-perceptible indication indicates that a shock is about to be delivered, and the second human-perceptible indication indicates that a confirmation process has been started; and then controlling the discharge circuit to deliver a shock responsive to the cardiac arrhythmia.

15. The medium of claim 14, in which
CA1 includes Ventricular Fibrillation.

16. The medium of claim 14, in which
CA1 includes Ventricular Tachycardia, where a heart rate of the patient has a value larger than a first heart rate threshold.

17. The medium of claim 14, in which
the physiological signal includes an ECG waveform, and a type of a cardiac arrhythmia is CA1 if its ECG waveform has an amplitude smaller than a threshold amplitude.

18. The medium of claim 14, in which
CA2 includes Ventricular Tachycardia, where a heart rate of the patient has a value less than a second heart rate threshold.

19. The medium of claim 14, in which
if a value of the heart rate of the patient is within a range, the type is determined to be CA1 or CA2 depending both on the value of the heart rate and on a value of a width of detected QRS complexes of the patient.

20. The medium of claim 14, in which
the physiological signal includes an ECG waveform, and a type of a cardiac arrhythmia is CA2 if its ECG waveform has an amplitude larger than a threshold amplitude.

21. The medium of claim 14, in which when the one or more programs are executed by the at least one processor, the operations further comprise:

causing an opening human-perceptible indication to be output responsive to detecting the cardiac arrhythmia, prior to completing the determination of the type.

22. The medium of claim 21, in which when the one or more programs are executed by the at least one processor, the operations further comprise:

determining whether or not the cardiac arrhythmia is validated according to a validation criterion, and in which the opening human-perceptible indication is caused to be output prior to completing the determination of whether the cardiac arrhythmia is so validated.

23. The medium of claim 14, in which
the user interface includes a first and a second output devices,
the first human-perceptible indication is output by the first output device, and
the second human-perceptible indication is output by the second output device.

24. The medium of claim 14, in which
the user interface includes a screen,
the first human-perceptible indication is a first image displayed by the screen, and
the second human-perceptible indication is a second image displayed by the screen that is different than the first image.

25. The medium of claim 14, in which
the user interface includes a speaker,
the first human-perceptible indication is a first sound message output by the speaker, and
the second human-perceptible indication is a second sound message output by the speaker that is different from the first sound message.

26. The medium of claim 14, in which
the user interface includes an output device that can cause a human-perceptible indication to be output at different intensity levels,
the first human-perceptible indication is output by the output device at a first intensity level, and
the second human-perceptible indication is output by the output device at a second intensity level that is different than the first intensity level by at least 20%.

* * * * *